(12) United States Patent
Takakura et al.

(10) Patent No.: US 7,109,321 B2
(45) Date of Patent: Sep. 19, 2006

(54) DNA FRAGMENT DIRECTING GENE EXPRESSION PREDOMINANT IN FLOWER ORGAN

(75) Inventors: Yoshimitsu Takakura, Shizuoka-ken (JP); Tsuyoshi Inoue, Shizuoka-ken (JP); Hideaki Saito, Shizuoka-ken (JP); Toru Ito, Shizuoka-ken (JP)

(73) Assignee: Japan Tobacco Inc., Tokyo (JP)

( * ) Notice: Subject to any disclaimer, the term of this patent is extended or adjusted under 35 U.S.C. 154(b) by 343 days.

(21) Appl. No.: 10/223,660

(22) Filed: Aug. 20, 2002

(65) Prior Publication Data

US 2003/0148320 A1   Aug. 7, 2003

Related U.S. Application Data

(63) Continuation of application No. 09/403,550, filed as application No. PCT/JP99/00568 on Feb. 10, 1999, now abandoned.

(30) Foreign Application Priority Data

Feb. 25, 1998   (JP)   .................................. 10-43372

(51) Int. Cl.
C12N 15/82   (2006.01)
(52) U.S. Cl. .................... 536/24.1; 435/320.1
(58) Field of Classification Search ............... 536/24.1; 435/320.1
See application file for complete search history.

(56) References Cited

FOREIGN PATENT DOCUMENTS

| EP | 0 913 469 | 5/1999 |
| JP | 6-504910 | 6/1994 |
| WO | 92/13956 | 8/1992 |
| WO | 98/29542 | 7/1998 |
| WO | 00/71704 A1 | 11/2000 |
| WO | 01/14543 A1 | 3/2001 |

OTHER PUBLICATIONS

Kim Y et al. A 20 nucleotide upstream element is essential for the nopaline synthase (nos) promoter activity. Plant Mol Biol. Jan. 24, 1994;(1):105-17.*
Eyal Y. et al. Pollen specificity elements reside in 30 bp of the proximal promoters of two pollen-expressed genes. Plant Cell. Mar. 7, 1995;(3):373-84.*
Hongtrakul et al., Helianthus annuus stearoyl-ACP desaturase mRNA, complete cds., Aug. 9, 1997, GenBank Accession U91339.*
Tsuchiya T. et al. Molecular characterization of rice genes specifically expressed in the anther tapetum. Plant Mol Biol. Dec. 26, 1994;(6):1737-46.*
Ingrid M. van der Meer et al., Plant Molecular Biology, vol. 15, pp. 95-109 (1990).
Genomics, vol. 10, No. 4 issued 1991, Werner Albig et al., pp. 940-948.
Journal of Virology, vol. 70, No. 1, issued Jan. 1996, Tai-An Cha et al , pp. 78-83 & Database GenBank, Accession No. U33331.
Database Genbank, Accession No. U91339, Aug. 9, 1997, Hongtrakul, V. et al.
Database GenBank, Accession No. AU029718, Oct. 19, 1998, Sasaki , T. and Yamamoto, K.
Plant Physiology, vol. 112, issued 1996, Rachel M. Hackett et al., pp. 1601-1607.
Plant Molecular Biology, vol. 35, No. 4, issued Nov. 1997, Michael Picker et al., pp. 425-431.
Mariani et al., *Nature*, vol. 347, 737-741 (Oct. 1990).
Goldman et al., *The EMBO Journal*, vol. 13, No. 13, 2976-2984 (1994).
Tsuchiya et al., *Plant Molecular Biology*, vol. 26, 1737-1746 (1994).
Takaiwa et al., *Plant Molecular Biology*, vol. 16, 49-58 (1991).
Dzelzkalns et al., *The Plant Cell*, vol. 5, 855-863 (Aug. 1993).
Mohan et al., *Plant Molecular Biology*, vol. 22, 475-490 (1993).
Gasser et al., *The Plant Cell*, vol. 1, 15-24 (Jan. 1989).
Corden et al., *Science*, vol. 209, 1406-1414 (Sep. 1980).
Zoller et al., *Nucleic Acids Research*, vol. 10, No. 20, 6487-6500 (1982).
Mikaelian et al., *Nucleic Acids Research*, vol. 20, No. 2, 376 (1992).

(Continued)

*Primary Examiner*—Cynthia Collins
(74) *Attorney, Agent, or Firm*—Birch, Stewart, Kolasch, and Birch, LLP

(57) ABSTRACT

An object of the present invention is to provide a novel DNA sequence having a flower organ-specific promoter activity which makes it possible to express a foreign gene specifically in pistil or lodicule, this enabling genetic manipulation. The present invention provides a DNA fragment comprising the sequence of positions 1 to 5369 in the nucleotide sequence represented by SEQ ID NO:3 in Sequence Listing, the sequence of positions 3335 to 5108 therein, a part of these sequences or a sequence derived from these sequences by deletion, substitution, insertion or addition of one or more nucleotides and having a promoter activity; and a flower organ-specific promoter sequence which can be identified from among sequences obtained by screening a genomic library of rice or other plants by using as a probe the nucleotide sequence as described above or a part thereof.

6 Claims, 8 Drawing Sheets

OTHER PUBLICATIONS

Zhou et al., *Nucleic Acids Research*, vol. 19, No. 21, 6052 (1991).
Heidecker et al., *Ann. Rev. Plant Physiol.*, vol. 37, 439-466 (1986).
Joshi, *Nucleic Acids Research*, vol. 15, No. 16, 6643-6653 (1987).
Kozak, *The Journal of Cell Biology*, vol. 108, 229-241 (Feb. 1989).
Komari et al., *The Plant Journal*, vol. 10, No. 1, 165-174 (1996).
Hiei et al., *The Plant Journal*, vol. 6, No. 2, 271-282 (1994).
Jefferson et al., *The EMBO Journal*, vol. 6, No. 13, 3901-3907 (1987).
Kim et al., *Plant Molecular Biology*, vol. 24 (1994) pp. 105-117.
Benfey et al., *Science*, vol. 250 (1990) pp. 959-966.
JP 11 098986A (Abstract only, Derwent Abstract No. XP002171917) (1999).
Greenland, AJ et al., *J. Cell. Biochem. Suppl.*, No. 14, Part E (1990) p. 348 (Derwent Listing only No. XP002171915).
Tsuchiya et al., *Plant and Cell Physiol.*, vol. 36, No. 3 (1995) pp. 487-494.
Ficker et al., *Mol. Gen. Genet.*, vol. 257 (1998) pp. 132-142.
Van der Leede-Plegt, LM et al., *Plant Cell Reports*, vol. 11, No. 1 (1992) pp. 20-24 (Abstract only, Derwent Abstract No. XP002171916).

\* cited by examiner

CTAATGACGG ATTAATTAGG CTTAATAAAT TCGTCTCACG TTTACTGACG GATTCTATAA
                                 213D
TTGATTTTTT TATTAATGCC CAAACACCCC ATACAACACT CTATATAATA CTCAATGTGA
           213C
CGTGCCAAAA CTTTAGACAC CTGGATGTAA ACACCACTCT GTTCCTTCTC CTCTATAAAT
  213B
GGCACCGGGG TGGTTTGTCG GCACCAAAGG CAGAAAAGAA AGCCAATGGC GTCTTCAGGC
                            213A
CTCGCAGTTG CAGCAACAGC CTCGTCAGCC TGGCTCTGCT GCCCCAATCA TCACATCCAT
              213Z-2                                          213Z
ACCAGCAGCA GCAGATCT
           BglII

Fig.4

SEQUENCE LISTING

<160> NUMBER OF SEQ ID NOS: 11

<210> SEQ ID NO 1
<211> LENGTH: 1524
<212> TYPE: DNA
<213> ORGANISM: Oryza sativa L.
<220> FEATURE:
<221> NAME/KEY: CDS
<222> LOCATION: (22)..(1275)

<400> SEQUENCE: 1

```
caaaggcaga aagaaagcc a atg gcg tct tca ggc ctc gca gtt gca gca        51
                      Met Ala Ser Ser Gly Leu Ala Val Ala Ala
                       1               5                  10 aca gcc tcg tca gcc tgg ctc tgc tgc ccc aat cat cac atc cat acc       99
Thr Ala Ser Ser Ala Trp Leu Cys Cys Pro Asn His His Ile His Thr
             15                  20                  25 agc agc agc aga tct cgc aag cat ctt ctt ctc cat ggc ctg tac ggg      147
Ser Ser Ser Arg Ser Arg Lys His Leu Leu Leu His Gly Leu Tyr Gly
                30                  35                  40 tct gca cct gca cgt act agg gga cga cgg ccg ccg gtg tgg act gcg      195
Ser Ala Pro Ala Arg Thr Arg Gly Arg Arg Pro Pro Val Trp Thr Ala
            45                  50                  55 gcg gcg gcc acc gca gca gcg ccg gcg gac acg gcg gcg tcg gcg cgg      243
Ala Ala Ala Thr Ala Ala Ala Pro Ala Asp Thr Ala Ala Ser Ala Arg
         60                  65                  70 cgg gag cag gtg gag atc gcc cgg tcg ctg aac gcg tgg gtg gag gag      291
Arg Glu Gln Val Glu Ile Ala Arg Ser Leu Asn Ala Trp Val Glu Glu
75                  80                  85                  90 aac atg ctc ccg ctg ctc acc ccc gtc gac tcc gcg tgg cag ccg cac      339
Asn Met Leu Pro Leu Leu Thr Pro Val Asp Ser Ala Trp Gln Pro His
                 95                 100                 105 gac ttc ctt ccc tgc tcg gcc gcg ggc ggc ggc gag gcg ctg gcg gcg      387
Asp Phe Leu Pro Cys Ser Ala Ala Gly Gly Gly Glu Ala Leu Ala Ala
            110                 115                 120 ttc acg gag ggc gtg gcc gag ctg cgc gcg ggc gcc gcc ggc gtg ccg      435
Phe Thr Glu Gly Val Ala Glu Leu Arg Ala Gly Ala Ala Gly Val Pro
        125                 130                 135 gac gag gtg ctg gtc tgc ctc gtg ggg aac atg gtg acg gag gag gcg      483
Asp Glu Val Leu Val Cys Leu Val Gly Asn Met Val Thr Glu Glu Ala
    140                 145                 150 ctc ccg acg tac cag agc atg ggc aac cgc gcc gag ggc ctc gcc gac      531
Leu Pro Thr Tyr Gln Ser Met Gly Asn Arg Ala Glu Gly Leu Ala Asp
155                 160                 165                 170 ggc acc ggc gtg agc ccc ctc ccc tgg gcg cgc tgg ctc cgc ggc tgg      579
Gly Thr Gly Val Ser Pro Leu Pro Trp Ala Arg Trp Leu Arg Gly Trp
                175                 180                 185 acc gcc gag gag aac cgc cac ggc gac ctc ctc aac cgc tac ctc tac      627
Thr Ala Glu Glu Asn Arg His Gly Asp Leu Leu Asn Arg Tyr Leu Tyr
            190                 195                 200 ctc tcc ggc cgc gtc gac atg cgc cag gtc gag gcc acc gtg cac cgc      675
Leu Ser Gly Arg Val Asp Met Arg Gln Val Glu Ala Thr Val His Arg
        205                 210                 215 ctc ctc cgc aac ggc atg gag atg ctg gcg ccg gcg agc ccg tac cac      723
Leu Leu Arg Asn Gly Met Glu Met Leu Ala Pro Ala Ser Pro Tyr His
```

-continued

```
                                                              220                 225                 230
ggc ctg atc tac ggc gcg ttc cag gag cgc gcc acc ttc atc tcc cac          771
Gly Leu Ile Tyr Gly Ala Phe Gln Glu Arg Ala Thr Phe Ile Ser His
235                 240                 245                 250 ggc cac acg gcg agg ctc gcg ggg cag cac ggc gac cgg gcg ctc gcc          819
Gly His Thr Ala Arg Leu Ala Gly Gln His Gly Asp Arg Ala Leu Ala
                255                 260                 265 aag atc tgc ggc gtg atc gcc gcc gac gag agg cgg cac gag gcg ggc          867
Lys Ile Cys Gly Val Ile Ala Ala Asp Glu Arg Arg His Glu Ala Gly
            270                 275                 280 tac acg atg gcg tcc gcc agg ctg ttc gag ctc gac ccg gac ggc atg          915
Tyr Thr Met Ala Ser Ala Arg Leu Phe Glu Leu Asp Pro Asp Gly Met
        285                 290                 295 gcg cgc gcg ctc gcg gac gtc atg cgc ggg aag gtg acc atg ccg ggg          963
Ala Arg Ala Leu Ala Asp Val Met Arg Gly Lys Val Thr Met Pro Gly
    300                 305                 310 cag ctc atg tcg gac ggc cgc gac ggc gac ggc gag cac agc ctg ttc         1011
Gln Leu Met Ser Asp Gly Arg Asp Gly Asp Gly Glu His Ser Leu Phe
315                 320                 325                 330 gcc cgg ttc tcc gcc gtg gcg gag cgc gcc ggc gtg tac acg gcg agg         1059
Ala Arg Phe Ser Ala Val Ala Glu Arg Ala Gly Val Tyr Thr Ala Arg
                335                 340                 345 gac tac ggc gaa ctc gtc gag cac ttc gtg cgg agg tgg cgg gtg gcg         1107
Asp Tyr Gly Glu Leu Val Glu His Phe Val Arg Arg Trp Arg Val Ala
            350                 355                 360 gag ctc gcg gcg ggg ctc tcc ggc gag ggc cga cgc gcg cag gag tac         1155
Glu Leu Ala Ala Gly Leu Ser Gly Glu Gly Arg Arg Ala Gln Glu Tyr
        365                 370                 375 ctg tgc ggg ttg gcg ccc aag atc cgg agg atg gag gag ctg gcc cac         1203
Leu Cys Gly Leu Ala Pro Lys Ile Arg Arg Met Glu Glu Leu Ala His
    380                 385                 390 cgg agg gcg gcc cgc atc gag ccc gct atg gcc cgt ttc agc tgg atc         1251
Arg Arg Ala Ala Arg Ile Glu Pro Ala Met Ala Arg Phe Ser Trp Ile
395                 400                 405                 410 ttc gat agg ccc gtc atg ctg ggc tgatcaaccc ggggcttcgg ttatggtttt        1305
Phe Asp Arg Pro Val Met Leu Gly
                415 atgggcccgt ttactgggct ctgcttgctc aaattataat aagctacatc gtgtgctaaa       1365 ataatttatc tttgttatta aggattcgtg tgagaaagct attttgtttt ctgtagcaag       1425 tttaggaatg taatgtaatg taatgaagcg gcaggacgac tgccatttga ttaagaaaag       1485 actcgcgctt gtttgtagtc caaaaaaaaa aaaaaaaa                               1524
```

<210> SEQ ID NO 2
<211> LENGTH: 418
<212> TYPE: PRT
<213> ORGANISM: Oryza sativa L.

<400> SEQUENCE: 2

```
Met Ala Ser Ser Gly Leu Ala Val Ala Ala Thr Ala Ser Ser Ala Trp
1               5                   10                  15

Leu Cys Cys Pro Asn His His Ile His Thr Ser Ser Ser Arg Ser Arg
                20                  25                  30

Lys His Leu Leu Leu His Gly Leu Tyr Gly Ser Ala Pro Ala Arg Thr
            35                  40                  45

Arg Gly Arg Arg Pro Pro Val Trp Thr Ala Ala Ala Thr Ala Ala
        50                  55                  60

Ala Pro Ala Asp Thr Ala Ala Ser Ala Arg Arg Glu Gln Val Glu Ile
```

```
                65                  70                  75                  80
Ala Arg Ser Leu Asn Ala Trp Val Glu Glu Asn Met Leu Pro Leu Leu
                    85                  90                  95

Thr Pro Val Asp Ser Ala Trp Gln Pro His Asp Phe Leu Pro Cys Ser
                100                 105                 110

Ala Ala Gly Gly Gly Glu Ala Leu Ala Ala Phe Thr Glu Gly Val Ala
                115                 120                 125

Glu Leu Arg Ala Gly Ala Ala Gly Val Pro Asp Glu Val Leu Val Cys
            130                 135                 140

Leu Val Gly Asn Met Val Thr Glu Glu Ala Leu Pro Thr Tyr Gln Ser
145                 150                 155                 160

Met Gly Asn Arg Ala Glu Gly Leu Ala Asp Gly Thr Gly Val Ser Pro
                165                 170                 175

Leu Pro Trp Ala Arg Trp Leu Arg Gly Trp Thr Ala Glu Glu Asn Arg
                180                 185                 190

His Gly Asp Leu Leu Asn Arg Tyr Leu Tyr Leu Ser Gly Arg Val Asp
            195                 200                 205

Met Arg Gln Val Glu Ala Thr Val His Arg Leu Leu Arg Asn Gly Met
210                 215                 220

Glu Met Leu Ala Pro Ala Ser Pro Tyr His Gly Leu Ile Tyr Gly Ala
225                 230                 235                 240

Phe Gln Glu Arg Ala Thr Phe Ile Ser His Gly His Thr Ala Arg Leu
                245                 250                 255

Ala Gly Gln His Gly Asp Arg Ala Leu Ala Lys Ile Cys Gly Val Ile
            260                 265                 270

Ala Ala Asp Glu Arg Arg His Glu Ala Gly Tyr Thr Met Ala Ser Ala
            275                 280                 285

Arg Leu Phe Glu Leu Asp Pro Asp Gly Met Ala Arg Ala Leu Ala Asp
    290                 295                 300

Val Met Arg Gly Lys Val Thr Met Pro Gly Gln Leu Met Ser Asp Gly
305                 310                 315                 320

Arg Asp Gly Asp Gly Glu His Ser Leu Phe Ala Arg Phe Ser Ala Val
                325                 330                 335

Ala Glu Arg Ala Gly Val Tyr Thr Ala Arg Asp Tyr Gly Glu Leu Val
            340                 345                 350

Glu His Phe Val Arg Arg Trp Arg Val Ala Glu Leu Ala Ala Gly Leu
        355                 360                 365

Ser Gly Glu Gly Arg Arg Ala Gln Glu Tyr Leu Cys Gly Leu Ala Pro
    370                 375                 380

Lys Ile Arg Arg Met Glu Glu Leu Ala His Arg Arg Ala Ala Arg Ile
385                 390                 395                 400

Glu Pro Ala Met Ala Arg Phe Ser Trp Ile Phe Asp Arg Pro Val Met
                405                 410                 415

Leu Gly

<210> SEQ ID NO 3
<211> LENGTH: 5396
<212> TYPE: DNA
<213> ORGANISM: Oryza sativa L.
<220> FEATURE:
<221> NAME/KEY: CDS
<222> LOCATION: (5016)..(5161)
<220> FEATURE:
<221> NAME/KEY: CDS
<222> LOCATION: (5243)..(5396)
```

```
<400> SEQUENCE: 3
gagctcatgt gaccgttctc ggtgagttca gagataacgt ttagacttcc cttatcagcc      60
tcgtgcgggc acctataggg tttgtctgag tcaatctccg atgtcagcca agaaagaaca     120
gagcatacga gtaaatctcc cgtcttgctg taatcaagaa tttggattga agtcaagaaa     180
ttttatctcg gcaggtacac catctcttca ttccgtattc cttgtcgaga tccaccaacc     240
gttctcgagt gatcgagaag gtgtagaatc tgcgacggga ctttgtcgac atttgtcgta     300
ctcgccttag tcgatcttgg tgtagaacca tagagacatg gagccttcgt caatgtcgaa     360
tagaattttc ctgaaatcaa tactcataaa agaatattag atagaaataa cccccgagcg     420
aacgctcaaa gggtaacatg ttatacaatg tatggaaaac tgaaatgaa ttaaatttac      480 agaccaatgt tttgtatatg agcgtctact cttttaccga cttcgatcag tcaatttgtt     540
aagttatata ctttccctag cccctagcct tgtcgttgga aatcgttct cggaagataa      600 ggctcttgga ccttttgacct gcctcggttg aacaagcact aatcctagcc cccagccgtg    660
aagttggaaa acccgattc cgattacacg gcttggttaa tacgcacggc gagaactctt      720
acacgaccag atcttacatg gtcttttgtc tctacagtat ccgacaaggc cttattggct     780
ctgggcgtcc ccagccgaag ttcccttagg ttcctcggag gccttgtcaa gacggtgtaa     840
agggacagta ggataggttt caacgctagg tgtcatcgtg gtaagggatc tctgggtaaa     900
acacttggcg atcttgtgta cctgatatca actttgttgg agtaaaggta atgggagaat     960
cgctacacct ctggttgagg accaggtggt agtcgcaact cgaccacttg aagtagaaat    1020
agtgggagaa tcgctacacc gctggtcgag aaccaagtag tagtctaaac tcgaccacta    1080
gaattaaagg tagtgggaga atcgctacac cgctggtcga aactaggta tagtctaaac     1140 tcgaccacta gaagtaaagg tagtgggaga atcgctacac cgctggtcga ggaccaggta    1200
gtagtcgtaa ctcgaccact agaagtggaa atagtgggag aatcgctaca ccgctggtcg    1260
agaaccaggt gtaatctaaa ctcgaccact tgaagtaaat gtgcgagaga tcgctacgat    1320
tgacgggtct agaaccagtg agtaggtgtc tctcaaccat cttaagtcat ggtgcgagga    1380
ctgctgcgtt attgctgtag tcgtacctcg accatctaaa gttaaggtgc gagagattgc    1440
tacgttttac tagttcaaga accagcgagc gagtagaatt atctctcgaa caccaatgaa    1500
agttgcggtg cgagagattg ctacgtactg gttcgaggac catcgagcga gtagaattat    1560
ctctcgaaca ccaatggaag ttgcggtgcg agagatttct acgtactggt tcgagaacca    1620
gcgagcgagt agaatcatct ctcgaacacc aatggaggtt gcggtgcgaa agattaatat    1680
gcactggttc gaggaccagc gaacgtgtag agttatatct cgaacaccaa tggaagttgc    1740
ggtgcgagag attgctacgt actagttcga ggaccatcga gcgagtagaa ttatttctcg    1800
aacaccaatg gaagttgcgg tgcgagagat tgctacgtac tggttcgaga accagcgagc    1860
gagtagaatt atctctcgaa caccaatgga gtttgcggt gcgagagatt gctacgtact     1920
ggttcaagaa ccatggaagt tgcggtgcga gagatttcta tgtactggtt cgaggaccag    1980
ggagcgagta gaattatctc tcgaacacca atggaagttt gcggtgcgag agattgctac    2040
gtactggttc gagaaccagt gaatgtgtag agttatctct cgaacaccaa tggaggttgc    2100
ggtgcgagag attgctacgt actggttcga gaaccagcga acgtgtagag ttatctctcg    2160
aacacatgga ggttgcggtg cgagagattg ctacgtactg gttcgaggac cagtgaacgt    2220
gtagagttat ctctcgaaca ccaatggagg tgctagagtt ggtttattac atatgcgtct    2280
catgtggcca gcatgactca cacacccaac ttgtagcata tccggatgtc tgttcgcaag    2340
```

```
catgtcgggt gatcaagccg acagcgctcg cgaggaatta tccgttaaca accttttctc      2400
gagtagtcta gccatggcgg gtgctatgag ataggtcgtc ggtcttcgtt ggtgggttgg      2460
gcgtgacgac tttgcatttg tcgagatcgt tctcgataat gcggtgtact tgaccacaac      2520
ctagtcgagt gctcaattgt tcctgaaaaa tattttctag aagacaagac atatagcaga      2580
taatatcgag tatgtactca gaaaactgca tggatcttct agtattatca ggatgtaacg      2640
agcagatgta aatattaggc attatgtaaa ccgtaaacaa gcatgattca tacaaaagag      2700
aatagagcga gccccagtgt tagaccgttg tcggcctaac accggaaaca ctcacataat      2760
aaatattgta taaaaaacat gctctaggta aacataataa attatattat agatctgaca      2820
attctgtatg atctgaatag gtacgataaa ttgcatataa aatattgcgt accttttgtag     2880 atacatgccg gatgtatcta cgaaattagt agattcaatc tactgaatac ctttgccttc      2940
ttggtgagga acagcaactc cttaatatgc ttttgcgtgc atggtactgt cccccgtgca      3000
cgtaccatgt aatctggtca tttaattgac ctgtttgtct ttagcccga gtcagattgc       3060 tgcctagaga ttggatagta gtgcagacgt ggaaactccc cgagtccgac tagcatttac      3120
accaataagc agatcaatcc gacgctttga tttccgctcc acgacgcgct tgttttgttg      3180
gtggagatcg atgccgtgtt cggcttggac gcggttaatc gagccctcca ccagttgatg      3240
tggcgcgtgt attggtactg atcaatctcg aaggttgtct gcactgttga ttgacaacct      3300
caaaattgac gtgatccacg gcattgacgt cttgaagctt gagcgatcct gataaatcga      3360
atttgttgac gacgattgtt ccgatctcgt cgggacacgt attctggtag gtttagatca      3420
cccaacagcg aagttgtcga gtagattgtt gtcggagaat ccatctctta aacccatctc     3480
gtcgaaatcc tgaagcacca aaatccccct acctggcgtg ccattatcga cgtttgatgt     3540
ctcgactacg gtatttgcat gtcatggggg atcgttggta ctaggatata cgcgagactg     3600
acgtaaaaga gatggagaca gggatttttta tacaggttcg ggcccctgaa ttgtcatata      3660
ataaccctac atcctgttgg ccgaagccgg tattgctctt attcatgata atcacaccat      3720 tacaatatt agggtagcct atctaactat tgtcgacatg gcggtctgac gatctgactc        3780
gtagtcgaca acagggtagc cttcctcctc gaacctgtgc ctgacgagat cagagatagc      3840
gctttcgtct ctcctgacag tatcctgaga caccgtaggg gacttgtcgt gcctatctct      3900
gaagtcgata tccggcgtct tgtcttggcg tatgttggct tgtattggct tgtggctttg      3960
tggcgtttat gttgctcgta tattgtggtg ggtgtgtatt gtccgtgtct tgtatggtgg      4020
gtgtcgattg tgtcccattt ccttctaggg gaccttgtat ttatacccat aggtgtcccc      4080
ttgtccaagt agaactaggg aaaccaatat ggatacaatc cgattagtcc tttgtcgttt      4140
ccatgtagaa ctttggttgt ctttctttat ccggaactcc tcctatatcc gcaggttatt      4200
ttcgtatagg acatgttatg tggtgggtcc taccgagatt tagtcaacta ctattaggta      4260
tgtggtatcc ataaccctga cacataccat gattttctg tctatcaata actgcctcgg       4320
tgaacttgaa gaagtaggtt gttattgcag caataatgag acaaactagt atttattttat     4380 gatatccctt ggttaagtag tcatgcgtta taataggaac ctctaattcc ctcgtaaata      4440
cagctaagtt tattataaca agagcttaa taatattaaa attgtagcct tttttggatt       4500
tgtacgaaat aattagcctt aaaaaacatt taatgttggt tagctcaaaa tatttggaaa      4560
tggagtgagt atatgttact gacttcaaaa attttttcaaa cggtattcat gtcgttttcg     4620
tgagtggact gaaacagcag taattacatt gaacatttga acacctgtat aaagtattaa      4680
```

```
atatatacta aaaaataatt aattatacat attacgacta atttgcaaga cgaatctttt    4740
aagcataatt gctccatgat ttaacaatat agtgctacag taaacatgtg ctaatgacgg    4800
attaattagg cttaataaat tcgtctcacg tttactgacg gattctataa ttgattttt     4860 tattaatgcc caaacacccc atacaacact ctatataata ctcaatgtga cgtgccaaaa    4920
ctttagacac ctggatgtaa acaccactct gttccttctc ctctataaat ggcaccgggg    4980
tggtttgtcg gcaccaaagg cagaaaagaa agcca atg gcg tct tca ggc ctc      5033
                                       Met Ala Ser Ser Gly Leu
                                        1               5 gca gtt gca gca aca gcc tcg tca gcc tgg ctc tgc tgc ccc aat cat      5081
Ala Val Ala Ala Thr Ala Ser Ser Ala Trp Leu Cys Cys Pro Asn His
         10              15                  20 cac atc cat acc agc agc agc aga tct cgc aag cat ctt ctt ctc cat      5129
His Ile His Thr Ser Ser Ser Arg Ser Arg Lys His Leu Leu Leu His
     25                  30                  35 ggc ctg tac ggg tct gca cct gca cgt act ag  gtatagtagc tgcaactta     5181
Gly Leu Tyr Gly Ser Ala Pro Ala Arg Thr Arg
     40                  45 ttcacaatgt gatgtcacgt tattatatat gtttcgtcgt caatggcggc gaaccttgca    5241
g g gga cga cgg ccg ccg gtg tgg act gcg gcg gcc acc gca gca          5288
  Gly Arg Arg Pro Pro Val Trp Thr Ala Ala Ala Thr Ala Ala
       50                  55                  60 gcg ccg gcg gac acg gcg gcg tcg gcg cgg cgg gag cag gtg gag atc      5336
Ala Pro Ala Asp Thr Ala Ala Ser Ala Arg Arg Glu Gln Val Glu Ile
65              70                  75                  80 gcc cgg tcg ctg aac gcg tgg gtg gag gag aac atg ctc ccg ctg ctc      5384
Ala Arg Ser Leu Asn Ala Trp Val Glu Glu Asn Met Leu Pro Leu Leu
             85                  90                  95 acc ccc gtc gac                                                      5396
Thr Pro Val Asp
            100

<210> SEQ ID NO 4
<211> LENGTH: 100
<212> TYPE: PRT
<213> ORGANISM: Oryza sativa L.

<400> SEQUENCE: 4

Met Ala Ser Ser Gly Leu Ala Val Ala Ala Thr Ala Ser Ser Ala Trp
1               5                   10                  15

Leu Cys Cys Pro Asn His His Ile His Thr Ser Ser Ser Arg Ser Arg
            20                  25                  30

Lys His Leu Leu Leu His Gly Leu Tyr Gly Ser Ala Pro Ala Arg Thr
        35                  40                  45

Arg Gly Arg Arg Pro Pro Val Trp Thr Ala Ala Ala Thr Ala Ala
    50                  55                  60

Ala Pro Ala Asp Thr Ala Ala Ser Ala Arg Arg Glu Gln Val Glu Ile
65              70                  75                  80

Ala Arg Ser Leu Asn Ala Trp Val Glu Glu Asn Met Leu Pro Leu Leu
                85                  90                  95

Thr Pro Val Asp
            100

<210> SEQ ID NO 5
<211> LENGTH: 20
<212> TYPE: DNA
<213> ORGANISM: Artificial
<220> FEATURE:
```

-continued

<223> OTHER INFORMATION: Primer 213S directed to Oryza sativa

<400> SEQUENCE: 5
cgctatggcc cgtttcagct                    20

<210> SEQ ID NO 6
<211> LENGTH: 21
<212> TYPE: DNA
<213> ORGANISM: Artificial
<220> FEATURE:
<223> OTHER INFORMATION: Primer 213AS directed to Oryza sativa

<400> SEQUENCE: 6
gtcgtcctgc cgcttcatta c                  21

<210> SEQ ID NO 7
<211> LENGTH: 19
<212> TYPE: DNA
<213> ORGANISM: Artificial
<220> FEATURE:
<223> OTHER INFORMATION: Primer 213Z directed to Oryza sativa

<400> SEQUENCE: 7
tgctggtatg gatgtgatg                     19

<210> SEQ ID NO 8
<211> LENGTH: 18
<212> TYPE: DNA
<213> ORGANISM: Artificial
<220> FEATURE:
<223> OTHER INFORMATION: Primer 213Z-2 directed to Oryza sativa

<400> SEQUENCE: 8
ctgacgaggc tgttgctg                      18

<210> SEQ ID NO 9
<211> LENGTH: 22
<212> TYPE: DNA
<213> ORGANISM: Artificial
<220> FEATURE:
<223> OTHER INFORMATION: Primer 213P-5H-2 directed to Oryza sativa

<400> SEQUENCE: 9
gacgtgatcc acggcattga cg                 22

<210> SEQ ID NO 10
<211> LENGTH: 27
<212> TYPE: DNA
<213> ORGANISM: Artificial
<220> FEATURE:
<223> OTHER INFORMATION: Primer 213P 2ndATG-Bam directed to Oryza sativa

<400> SEQUENCE: 10
cggggatccg ttctcctcca cccacgc            27

<210> SEQ ID NO 11
<211> LENGTH: 318
<212> TYPE: DNA
<213> ORGANISM: Oryza sativa

<400> SEQUENCE: 11
ctaatgacgg attaattagg cttaataaat tcgtctcacg tttactgacg gattctataa      60
ttgatttttt tattaatgcc caaacacccc atacaacact ctatataata ctcaatgtga     120
cgtgccaaaa ctttagacac ctggatgtaa acaccactct gttccttctc ctctataaat     180

```
ggcaccgggg tggtttgtcg gcaccaaagg cagaaaagaa agccaatggc gtcttcaggc      240
ctcgcagttg cagcaacagc ctcgtcagcc tggctctgct gccccaatca tcacatccat      300
accagcagca gcagatct                                                   318
```

DNA FRAGMENT DIRECTING GENE EXPRESSION PREDOMINANT IN FLOWER ORGAN

This application is a continuation of application Ser. No. 09/403,550, filed on Dec. 1, 1999 now abandoned and for which priority is claimed under 35 U.S.C. § 120. Application Ser. No. 09/403,550 is the national phase of PCT International Application No. PCT/JP99/00568 filed on Feb. 10, 1999 under 35 U.S.C. § 371. The entire contents of each of the above-identified applications are hereby incorporated by reference. This application also claims priority of Application No. 43372/1998 filed in JAPAN on Feb. 25, 1998 under 35 U.S.C. § 119.

TECHNICAL FIELD

This invention relates to a promoter capable of directing the expression of a foreign gene specifically in flower organs.

1. Prior Art

Although there have been reported several genes expressed in flower organs including anther-specific genes and pistil-specific ones, the promoter sequences of these genes are poorly understood. Regarding dicotyledons, Mariani et al. (Nature, 347, 737–741, 1990) report analysis on the expression site of a promoter of a tobacco anther tapetal cell-specific gene TA29, while Goldman et al. (The EMBO Journal 13, 2976–2984, 1994) report the isolation of a tobacco pistil stigma-specific gene STIG1 and analysis on the expression site of its promoter. In these reports, it is also stated that male sterile and female sterile tobacco plants were constructed each by linking a bacterial RNase to the promoter and transferring it into plant cells, thus providing an example of artificial manipulations of physiological and morphological characteristics with the use of a tissue-specific promoter. Regarding monocotyledons, on the other hand, there have been reported some cases of the isolation of anther-specific promoters but no pistil-specific promoter so far. For example, JP (Kohyo) HEI 6-504910 reports the isolation of a rice anther-specific gene, its promoter and use thereof, while Tsuchiya et al. (Plant Mol. Biol. 26, 1737–1746, 1994) report analysis on the expression of a rice immature anther tapetal cell-specific promoter.

Promoters exhibiting expression specifically in flower organs are desired in order to artificially improve the morphology of plant flower organs, in particular, germ organs or physiological phenomena or to analyze functions of various genes in flower organs. In monocotyledons which represent major cereals, however, few genes expressed exclusively in flower organs have been isolated hitherto. In particular, there has been reported no promoter sequence showing predominant expression in pistil which is the female germ organ or lodicule which regulates flowering.

2. Disclosure of the Invention

An object of the present invention is to provide a novel DNA sequence having a flower organ-specific promoter activity which makes it possible to express a foreign gene specifically in pistil or lodicule, thus enabling genetic manipulations which were impossible in the prior art particularly in monocotyledons.

To achieve the above-described object, the present inventors have conducted extensive research and, as a result, succeeded in the isolation and identification of a clone showing flower organ-specific expression through a differential screening of a paddy rice pistil cDNA library with the use of a pistil probe and a leaf probe, thus completing the present invention.

In the first aspect, the present invention provides a DNA fragment comprising the sequence of positions 3335 to 5108 in the nucleotide sequence represented by SEQ ID NO: 3 in Sequence Listing, a part of said sequence or a sequence derived from said sequence by deletion, substitution, insertion or addition of one or more nucleotides and having a promoter activity.

In a preferred embodiment of the present invention, it provides a DNA fragment wherein a part of the sequence of positions 3335 to 5108 in the nucleotide sequence represented by SEQ ID NO:3 is located downstream of the point of at least 500 nucleotides upstream of the transcription initiation points (the nucleotides of positions 4995 to 4997 in the nucleotide sequence represented by SEQ ID NO:3).

In another preferred embodiment of the present invention, a DNA fragment is provided wherein a part of the sequence of positions 3335 to 5108 in the nucleotide sequence represented by SEQ ID NO:3 is located in the region upstream of the first initiation codon (the nucleotides of positions 5016 to 5018 in the nucleotide sequence represented by SEQ ID NO:3).

In another preferred embodiment of the present invention, a DNA fragment is provided wherein the region upstream of the initiation codon is located downstream of the point of at least 500 nucleotides upstream of the transcription initiation points.

In another preferred embodiment of the present invention, a DNA fragment is provided wherein a part of the sequence of positions 3335 to 5108 in the nucleotide sequence represented by SEQ ID NO:3 is located in the region upstream of transcription initiation points (the nucleotides of positions 4995 to 4997 in the nucleotide sequence represented by SEQ ID NO:3).

In another preferred embodiment of the present invention, a DNA fragment is provided wherein the region upstream of the transcription initiation points is the region of at least 500 nucleotides upstream of the transcription initiation points.

In another preferred embodiment of the present invention, a DNA fragment is provided comprising the sequence of positions 3335 to 5108 in the nucleotide sequence represented by SEQ ID NO:3 in Sequence Listing or a sequence derived from the above sequence by deletion, substitution, insertion or addition of one or more nucleotides and having a promoter activity.

In the second aspect, the present invention provides a DNA fragment comprising the sequence of positions 1 to 5369 in the nucleotide sequence represented by SEQ ID NO:3 in Sequence Listing, a part of said sequence or a sequence derived from said sequence by deletion, substitution, insertion or addition of one or more nucleotides and having a promoter activity.

In a preferred embodiment of the present invention, a DNA fragment is provided wherein a part of the sequence of positions 1 to 5369 in the nucleotide sequence represented by SEQ ID NO:3 is located downstream of the HindIII site (the nucleotides of positions 3335 to 3340 in the nucleotide sequence represented by SEQ ID NO:3).

In another preferred embodiment of the present invention, a DNA fragment is provided wherein a part of the sequence of positions 1 to 5369 in the nucleotide sequence represented by SEQ ID NO:3 is located downstream of the point of at least 500 nucleotides upstream of transcription initiation points (the nucleotides of positions 4995 to 4997 in the nucleotide sequence represented by SEQ ID NO:3).

In another preferred embodiment of the present invention, a DNA fragment is provided wherein a part of the sequence of positions 1 to 5369 in the nucleotide sequence represented by SEQ ID NO:3 is located upstream of the third BglII site (the nucleotides of positions 5103 to 5108 in the nucleotide sequence represented by SEQ ID NO:3).

In another preferred embodiment of the present invention, a DNA fragment is provided wherein a part of the sequence of positions 1 to 5369 in the nucleotide sequence represented by SEQ ID NO:3 is located in the region upstream of the first initiation codon (the nucleotides of positions 5016 to 5018 in the nucleotide sequence represented by SEQ ID NO:3).

In another preferred embodiment of the present invention, a DNA fragment is provided wherein a part of the sequence of positions 1 to 5369 in the nucleotide sequence represented by SEQ ID NO:3 is located upstream of the transcription initiation points (the nucleotides of positions 4995 to 4997 in the nucleotide sequence represented by SEQ ID NO:3).

In another preferred embodiment of the present invention, a DNA fragment is provided comprising the sequence of positions 1 to 5369 in the nucleotide sequence represented by SEQ ID NO:3 in Sequence Listing or a sequence derived from said sequence by deletion, substitution, insertion or addition of one or more nucleotides and having a promoter activity.

In the third aspect, the present invention provides a chimeric DNA sequence comprising a DNA fragment of the present invention having a promoter activity as described above and a desired structural gene under the regulation of the same.

In the fourth aspect, the present invention provides a transformation vector having a chimeric DNA sequence according to the present invention as described above.

In the fifth aspect, the present invention provides a DNA fragment having a flower organ-specific promoter activity which is hybridizable with the sequence of positions 1 to 5369 in the nucleotide sequence represented by SEQ ID NO:3 in Sequence Listing or a part of the sequence having a flower organ-specific promoter activity. In a preferred embodiment of the present invention, hybridization is performed under conditions with a moderate hybridization intensity.

In the sixth aspect of the present invention, a flower organ-specific promoter sequence is provided which can be identified on the basis of a DNA sequence obtained by screening a genomic DNA library of rice or other plants by using as a probe the nucleotide sequence represented by SEQ ID NO:1 in Sequence Listing or a part of said sequence. In a preferred embodiment of the present invention, screening is performed under conditions with a moderate hybridization intensity.

In the seventh aspect of the present invention, a DNA fragment is provided comprising a sequence having at least 15 consecutive nucleotides in the sequence from positions 22 to 1278 of the sequence represented by SEQ ID NO:1 in Sequence Listing or a nucleotide sequence complementary to said sequence.

BRIEF DESCRIPTION OF THE DRAWINGS

FIG. 4 is a drawing illustrating the nucleotide sequence (SEQ ID NO:11) around the transcription initiation points.

PREFERRED MODE FOR CARRYING OUT THE INVENTION

Figure 1:
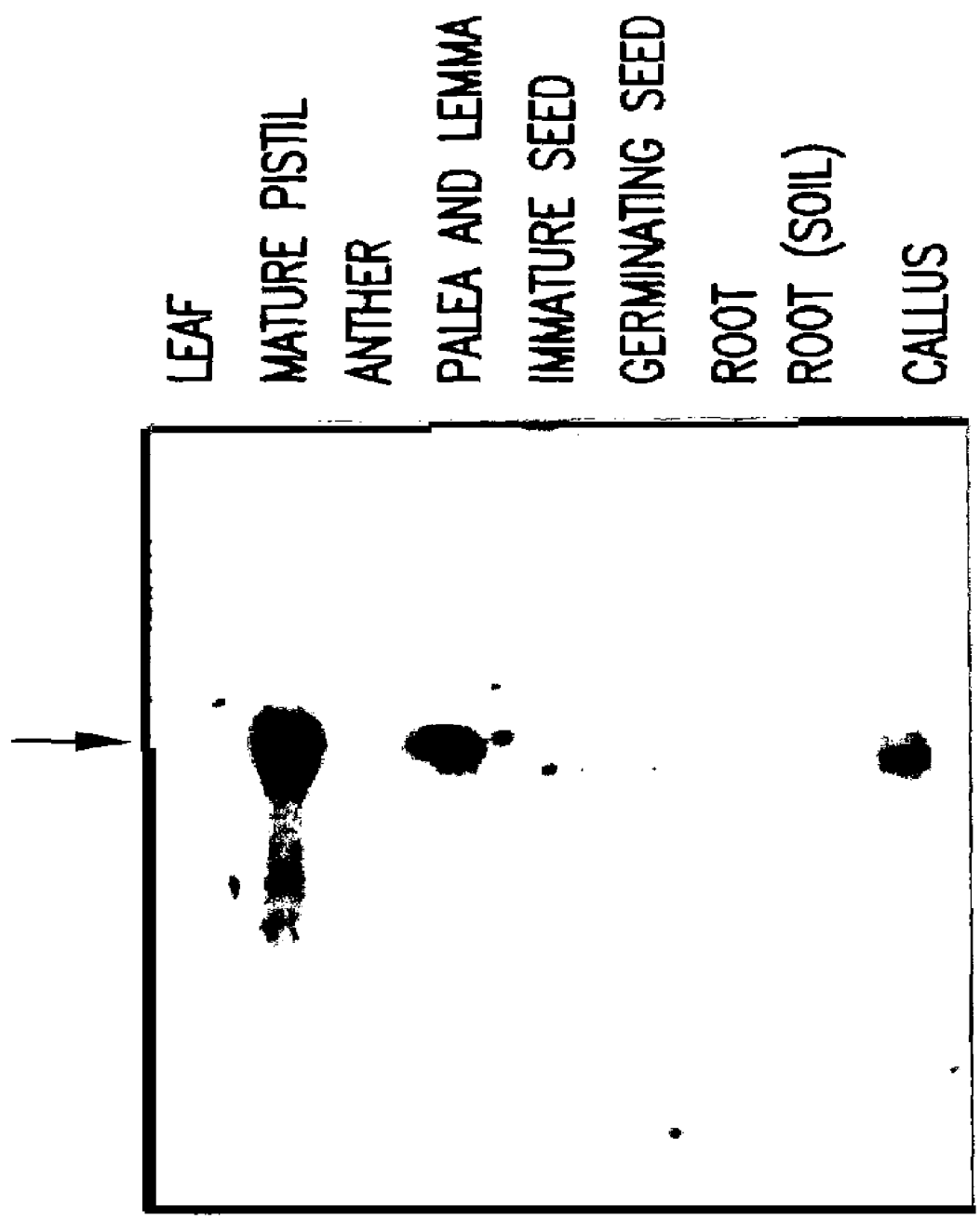
FIG. 1 is a photograph showing the results of Northern analysis on RPC213.

Now, the present invention will be described in greater detail.

As described above, one of the inventions produced by the present inventors relates to a DNA fragment comprising the sequence of positions 1 to 5369 in the nucleotide sequence represented by SEQ ID NO:3 in Sequence Listing, the sequence of positions 3335 to 5108 therein, a part of said sequences or a sequence derived from said sequences by deletion, substitution, insertion or addition of one or more nucleotides and having a promoter activity.

The promoter sequence of the present invention, namely, the sequence comprising the nucleotides of positions 1 to 5369 in the sequence represented by SEQ ID NO: 3 has no homology to any known promoter sequence. Thus, this sequence is considered to be a novel promoter sequence.

The DNA fragment of the present invention has a promoter activity specific to flower organs. The term "flower organ-specific promoter activity" as used herein means that the expression of the promoter activity of the DNA fragment of the present invention in flower organs (immature pistil in earing period, mature pistil in flowering period, lodicule, and palea and lemma) is more prominent than in other organs. In the reverse transcription PCR experiment performed in Examples as will be shown hereinafter, the expression levels in the organs other than these flower organs were less than 1/100 of the expression level in immature pistil. In this case, examination was made of anther in flowering period, leaf and root about 1 month after sowing, immature seed 1 to 2 weeks after fertilization, germinating seed, and callus, in addition to the three flower organs as described above (FIGS. 1 and 2, Table 1).

The nucleotide sequence represented by SEQ ID NO:3 in Sequence Listing has the following characteristics.

1. It has 3 consecutive transcription initiation points consisting of nucleotides, from upstream, C (cytosine), A (adenine) and A (adenine) (i.e., nucleotides of positions 4995 to 4997 in the sequence represented by SEQ ID NO:3).

2. There is a TATA box-like sequence (5'-TATAAA-3') (nucleotides of positions 4964 to 4969 in the sequence represented by SEQ ID NO:3) (Corden et al. Science 209, 1406–1414, 1980) 31 bp upstream of the most upstream transcription initiation point C (cytosine).

3. The first initiation codon ATG (nucleotides of positions 5016 to 5018 in the sequence represented by SEQ ID NO:3) is located 21 bp downstream of the most upstream transcription initiation point C (cytosine).

4. The second ATG is located in the same reading frame 273 bp downstream of the first initiation codon, while an intron sequence of 81 bp is located between them.

In the present invention, regions upstream of the presumed structural gene regions (although we do not exclude a possibly that these regions may include some part of the 5'-terminus region of the structural gene), namely, the sequence consisting of the nucleotides of positions 1 to 5369 and the sequence consisting of the nucleotides of positions 3335 to 5108 in the nucleotide sequence represented by SEQ ID NO:3 are specified as promoter sequences. Moreover, sequences comprising a part of these sequences fall within the scope of the present invention, so long as they have promoter activity. For example, it is expected that the region of positions 1 to 4994 and the region of positions 3335. to 4994 have a promoter activity, since the transcription initiation point is located at position 4995 as described above.

Moreover, said latter sequence consisting of the nucleotides of positions 3335 to 5108 in SEQ ID NO:3 was specified as a promoter sequence, since a HindIII cleavage site is located at position 3335 by chance. Therefore, it is well anticipated that a sequence starting from a nucleotide somewhat downstream will have the promoter activity too. This is so because a number of reports indicate that the tissue—or time-specificity or inducibility of most plant promoters is sustainedlly contained in the region of 0.3 to 0.4 kbp which precedes the transcription initiation point. In the promoter of type II glutelin gene of rice, for example, the tissue—and time-specific expression in albumen was fully achieved by a 441 bp fragment of the upstream region of the transcription initiation point (Takaiwa et al. Plant Mol. Biol. 16:49–58, 1991). In the promoter of self-incompatibility-related gene SLG13 of *Brassia oleracea*, the 411 bp upstream region of the transcription initiation point directed the expression in pistil and pollen (Dzelkalns et al. The Plant Cell 5: 855–863, 1993). In the promoter of anionic peroxidase gene of tomato, the organ-specificity as well as the pathogen and wound-inducibility were determined by the 358 bp upstream region of the transcription initiation point (Mohan et al. Plant Mol. Biol. 22: 475–490, 1993). Thus, it is observed in a number of promoters that a part of the reported nucleotide sequence maintains the full function as a promoter, in particular, the specificity, if only said part is the region located within several hundred bp upstream of the transcription initiation point.

Accordingly, any sequence comprising a DNA fragment from the region within several hundred bp, preferably about 500 bp, upstream of the transcription initiation points and having the flower organ-specificity characterized in the present invention is included in the scope of the present invention. For example, if a region within several hundred bp upstream of the transcription initiation point or a region containing the same is easily isolated from rice genome by PCR with the use of primers designed based on the nucleotide sequence of the present invention and the region exhibits the flower organ-specificity inherent to the promoter of the present invention, then the shorter promoter sequence is included in the scope of the present invention.

The DNA fragment of the present invention can be obtained by, for example, starting with rice by the methods as will be described in the following Examples. Alternatively, it can be easily prepared by PCR with the use of rice genome as a template by using as primers a pair of oligonucleotides corresponding respectively to both termini of the DNA fragment of the present invention the nucleotide sequence of which has been clarified. In order to determine whether or not the sequence has flower organ-specificity, a chimera gene can be constructed by ligating β-glucuronidase (GUS) gene to the promoter sequence and the resultant chimera gene is introduced into rice plant to thereby confirm the expression sites.

The present invention further includes in its scope DNA fragments having a sequence derived from these sequences by deletion, substitution, insertion or addition of one or more nucleotides and showing the promoter activity.

It is well known that when a nucleotide sequence of a DNA having a physiological activity is slightly modified by substitution, deletion, addition or insertion of one or more nucleotides in the nucleotide sequence thereof, the physiological activity of the DNA is maintained in general. Therefore, the present invention includes within the scope thereof DNA sequences derived from the above mentioned promoter sequence by such slight modification and having the promoter activity. That is to say, the sequence consisting of the nucleotides of positions 1 to 5369 in the nucleotide sequence represented by SEQ ID NO:3 in Sequence Listing, the sequence consisting of the nucleotides of positions 3335 to 5108 therein, parts of these sequences having the promoter activity (for example, those consisting of a several hundred bp region upstream of the transcription initiation points), and DNA sequences derived therefrom by deletion, substitution, insertion or addition of a small number of nucleotides and having the promoter activity are all intended to be included in the scope of the present invention.

Similarly, the sequence consisting of the nucleotides of positions 1 to 4994 in the nucleotide sequence represented by SEQ ID NO:3 in Sequence Listing, the sequence consisting of the nucleotides of positions 3335 to 4994 therein and DNA sequences derived therefrom by deletion, substitution, insertion or addition of a small number of nucleotides and having the promoter activity are included in the scope of the present invention.

The addition, insertion, deletion or substitution of nucleotides can be carried out by, for example, site-directed mutagenesis (see, for example, Nucl. Acids Res. 10:6487–6500, 1982) which is a well-known technique. The expression "one or more nucleotides" as used herein means nucleotides in such a number as to allow addition, insertion, deletion or substitution by the site-directed mutagenesis method.

Site-directed mutagenesis can be performed in the following manner with the use of, for example, a synthetic oligonucleotide primer which is complementary to the single-stranded phage DNA to be mutated except a specific discordance, i.e., the desired mutation. Namely, a complementary strand is synthesized by a phage with the use of the above-mentioned oligonucleotide as a primer. Next, a host bacterium carrying the phage is transformed by the double-stranded DNA thus obtained. The culture of the transformed bacterium is then plated onto agar and plaques containing the phage from a single cell are formed. Thus theoretically 50% of the newly formed colonies will contain the phage carrying the mutation in the single strand while the remaining 50% of the colonies have the original sequence. The plaques thus obtained are hybridized with a synthetic probe having been treated with kinase at such a temperature as to allow the hybridization of the plaques coinciding with the DNA having the desired mutation as described above but not with those having the original strands. Then the plaques hybridized with the probe are picked up and cultured to subsequently recover the DNA.

In addition to the above site-directed mutagenesis method, nucleotide(s) can be substituted, deleted, added or inserted into the promoter sequence while maintaining its activity by treating the gene with a mutagen or by selectively cleaving the gene and then deleting, adding or substituting the desired nucleotide(s) followed by ligation.

Also, the substitution, deletion, addition or insertion of specific nucleotide(s) may be conducted by the site-directed mutagenesis with the use of the PCR method (Mikaelian et al. Nucl. Acids Res. 20:376, 1992) or the random nucleotide substitution technique (Zhou et al. Nucl. Acids Res. 19:6052, 1991) by taking advantage of the low fidelity of Taq DNA polymerase.

Now, another invention found by the present inventors will be illustrated.

This invention relates to a flower organ-specific promoter sequence which can be identified from among sequences obtained by screening a genomic library of rice or other plants by using as a probe the nucleotide sequence represented by SEQ ID NO:1 in Sequence Listing or a part of said sequence.

The nucleotide sequence represented by SEQ ID NO:1 can be obtained by the differential screening method with the use of rice (IR24) as will be described in Examples hereinafter. Alternatively, it can be easily prepared by the PCR method with the use of a rice flower organ-derived cDNA or rice genome as a template by using as primers a pair of oligonucleotides corresponding respectively to both termini of the DNA fragment of the present invention the nucleotide sequence of which has been clarified.

Either the whole nucleotide sequence or a part thereof may be used as a probe.

The genome library can be constructed by using rice green leaf by, for example, the method which will be described in detail in Examples hereinafter, though the present invention is not limited thereto. A genomic fragment containing the promoter is prepared from the thus obtained library by using the above-described probe and thus the promoter sequence is identified. In order to determine whether or not the sequence has flower organ-specificity, a chimera gene can be constructed by ligating β-glucuronidase (GUS) gene to the promoter sequence and the resultant chimera gene is introduced into a desired plant to confirm the expression sites.

The promoter sequence thus obtained should have flower organ-specificity of such an extent comparable (at least being predominant in any flower organ) to the specificity as will be described in Example 3(2) hereinafter.

Finally, a probe for detecting a flower organ-specific promoter, which is another aspect of the present invention, will be illustrated.

The probe according to the present invention comprises a DNA fragment comprising a sequence having at least 15 consecutive nucleotides in the sequence from positions 22 to 1278 of the sequence represented by SEQ ID NO:1 in Sequence Listing or a nucleotide sequence complementary to said sequence. It is highly possible that this sequence of positions 22 to 1278 in the sequence represented by SEQ ID NO:1 or a nucleotide sequence highly homologous thereto will undergo the flower organ-specific expression as described above. By using this sequence or a part thereof as a probe in examining plant genomic DNA, therefore, a novel flower organ-specific promoter occurring in rice or other plants can be found out.

The probe is designed based on the above-mentioned sequence. It preferably has at least 15 consecutive nucleotides. There is no particular upper limit of its length up to the full length of the sequence as described above. The present invention also includes within the scope thereof sequences which are derived from a DNA fragment selected from those described above by addition, deletion, insertion or substitution of one or more nucleotides while being hybridizable with the above sequence or a sequence highly homologous thereto. The addition, deletion, insertion or substitution can be performed by the same methods as described above regarding the flower organ-specific promoter according to the present invention.

The probe of the present invention can be prepared by cleaving the DNA fragment represented by SEQ ID NO:1 in Sequence Listing, which is obtained by the method as will be described in detail in Examples hereinafter, with appropriate restriction enzymes. Alternatively, it can be prepared by the PCR method with the use of a sample comprising this sequence. It is also possible to synthesize a single-stranded DNA serving as a probe by a conventional method with the use of a marketed DNA synthesizer (for example, one manufactured by Perkin Elmer).

The probe according to the present invention can be labeled by a conventional method with, for example, a radioisotope. For example, the random priming labeling method is employed to label the probe with $^{32}P$, while the 5'-terminal labeling method with the use of phosphorylating enzyme is employed when a synthetic oligomer is used.

When the probe of the present invention is used, hybridization can be performed by a conventional method. In general, hybridization is carried out under conditions giving a moderate hybridization intensity, i.e., performing the hybridization and washing at room temperature to 50° C. at an appropriate ionic strength (for example, 0–50% formamide, 6×SSC, 1×Denhart's solution, etc.). The probe of the present invention is used in a genome library of the plant to be treated and then the genomic DNA of the plant thus hybridized is isolated. Next, the upstream region of this gene is identified to thereby give a novel flower organ-specific promoter.

The flower organ-specific promoter of the present invention is a novel flower organ-specific promoter sequence which makes it possible to genetically manipulate and improve pistil and lodicule. This was previously impossible particularly in monocotyledons. Thus, the promoter is useful for, e.g., the following purposes.

1) Improvement in fertilizability of female germ organs by ligating a structural gene capable of enhancing tolerance to stress (such as cold weather, drought, hot, etc.) to the promoter sequence of the present invention or a part thereof.
2) Creation of female sterile plants by ligating a structural gene capable of inducing sterility to the promoter sequence of the present invention or a part thereof.
3) Flower organ-specific proliferation or enlargement by ligating a structural gene capable of promoting proliferation or division of plant cells to the promoter sequence of the present invention or a part thereof.
4) Genetic regulation of flowering by means of the expression of the promoter of the present invention in lodicule.
5) Providing the whole flower organs or a particular site thereof (for example, pistil) with an improved tolerance by ligating a gene capable of inducing an improved tolerance to herbicides or diseases to the promoter sequence of the present invention or a part thereof.

To further illustrate the present invention in greater detail, and not by way of limitation, the following Examples are given.

EXAMPLES

Example 1

Isolation of Flower Organ-specific cDNA

Paddy rice varieties "Tsukinohikari" and "IR24" were grown in a greenhouse and subjected to the following experiments.

(1) Extraction of RNA

The leaf, immature pistil, mature pistil, anther, lodicule, palea and lemma, immature seed, germinating seed, root, callus and immature spikelet (4.5 to 6.0 mm in length) of "IR24" were collected, immediately frozen in liquid nitrogen and then stored at −80° C. The total RNA was extracted from these tissues by the SDS-polyphenol method (Watanabe and Price, Proc. Natl. Acad. Sci. USA, 79, 6304–6308, 1982) except that β-mercaptoethanol was added as an antioxidant to the extraction buffer to give a final concentration of 10% (V/V). The tissues to be used in the reverse transcription PCR experiment were treated with DNase I (FPLC pure, manufactured by Pharmacia) in the presence of RNase inhibitor (RNAguard, manufactured by Pharmacia), rather than being subjected to lithium chloride precipitation, so as to minimize the contamination with any trace amount of DNA. 0.375 µg/µl of the total nucleic acid and 1.75 U/µl of RNase inhibitor were added in a buffer (40 mM Tris-Cl pH 7.5, 6 mM $MgCl_2$) and 0.375 U/µl of DNase I (each expressed in the final concentration) was added thereto. After maintaining at 37° C. for 10 to 30 minutes, DNase I was inactivated by extraction with phenol/chloroform.

The leaf and root [expressed in root (soil) in FIG. 1] were collected from a plant grown for 1 month in a greenhouse after sowing. The immature pistil was collected from a plant 1 to 2 weeks before earing. The mature pistil, anther, lodicule and palea and lemma were collected from a plant immediately to several days before flowering. The immature seed was collected from a plant 1 to 2 weeks after flowering. The germinating seed and root were obtained from a plant aseptically grown on an N6 medium (Chu et al. Scientia Sinica, 18, 659–668, 1975) respectively for 1 and 3 weeks after sowing. The callus was induced from a seed in an N6 solid medium containing 2 mg/l of 2,4-D and then cultured before use in a liquid medium of the same composition under shaking for 3 weeks. The total RNA of the pistil and leaf was purified to provide polyA+RNA by using Oligotex-dT30 super (manufactured by Takara Shuzo Co., Ltd.) in accordance with the manufacturer's instructions.

(2) Construction of Pistil cDNA Library

About 1 µg of polyA+RNA isolated and purified from pistil was employed as a template to synthesize the cDNA by using ZAP-cDNA Synthesis Kit (manufactured by STRATAGENE). The determination of $^{32}P$ uptake ratio indicated that about 55 ng of the first strand cDNA of the pistil was reversely transcribed by the olig-dT priming, and about 72 ng of the second strand cDNA was synthesized directly from the first strand. The cDNA was connected to an EcoRI adapter in accordance with the manufacturer's instructions, digested with XhoI and then ligated into vector UniZAP XR. Next, the phage DNA was packaged into phage particles by using Giga pack Gold packaging extract (manufactured by STRATAGENE). The phage was transfected into E. coil PLK-F' host cells, which were then inoculated on a plate. The library size of the pistil cDNA library was calculated as $3 \times 10^6$ pfu.

(3) Differential Screening

Differential screening was carried out basically in accordance with the method of Gasser et al. (The Plant Cell 1, 15–24, 1989). About 2,000 pfu of the phage from the pistil cDNA library was infected into E. coil PKL-F' cells and the cells were plated on square Petri dishes (14×10 cm). For each plate, a replica filter was prepared with the use of a nylon membrane filter Hybond-N+ (manufactured by Amersham) and the filter was treated in accordance with the manufacturer's instructions. As the probes for hybridization, use was made of single-stranded cDNA synthesized from about 100 ng of the polyA+RNA (or about 2 µg of the total RNA) of pistil and leaf. To 2 µg of an RNA solution, 0.5 mM of d(ATG)TP, 10 mM of DTT and 1×M-MuLV buffer (manufactured by BRL) were added. Next, 30 ng/µl of Random DNA Hexamer (manufactured by Pharmacia) [or 80 ng/µl of Oligo dT Primer (manufactured by Amersham)] was added thereto (each expressed in the final concentration). After dissociating the secondary structure of the RNA by heating at 65° C. for 5 minutes, the primer was annealed at room temperature. After further adding 1.5 U/µl of RNase inhibitor (RNA guard manufactured by Pharmacia), 10 U/µl of reverse transcriptase M-MuLV (manufactured by BRL) and 4 µCi/µl of [α-$^{32}$P]dCTP (each expressed in the final concentration), the liquid reaction mixture of 20 µl in total was incubated at 37° C. for 1 hour.

Subsequently, dCTP (RI-unlabeled) was further added to give a final concentration of 0.5 mM and the reaction was continued for 30 minutes. The labeled DNA probe were purified by using Quick Spin Column G-50 Sephadex (manufactured by BOEHRINGER MANNHEIM). The probes were single-stranded by adding an equivalent amount of 2 N NaOH (final concentration: 1 N). The filter was first treated in a pre-hybridization buffer (0.25 M $Na_2HPO_4$, pH 7.2, 7% SDS, 1 mM EDTA, 1×Denhart's solution) at 68° C. for 10 minutes. Then the single-stranded probes (final concentration: 0.2-0.3×$10^7$ cpm/ml) and carrier DNA (a mixture of 0.1 mg/ml of salmon sperm DNA, 0.1 µg/ml of λDNA, 0.1 µg/ml of rice DNA) were added thereto and hybridization was performed at 68° C. overnight (16 to 24 hours). The filter was washed in the buffer (20 mM $Na_2HPO_4$, pH 7.2, 1% SDS, 1 mM EDTA) at room temperature twice and at 68° C. twice each for 15 minutes. Next, this filter was exposed to Kodak X-Omat Film at −70° C. for 4 to 5 days.

When about 30,000 plaques were examined, 198 plaques showing intense hybridization signals with the pistil probe but only weak signals with the leaf probe were selected by the primary screening. 152 clones among them were subjected to the secondary screening. To avoid intense background of plaque hybridization in this step and to efficiently perform screening, the following method was employed. First, the plaques selected by the primary screening were stored in 200 µl of SM buffer (0.1 M NaCl, 7 mM $MgSO_4$, 50 mM Tris-CL pH 7.5, 0.01% gelatin) containing one drop of chloroform at 4° C. Then the thus stored liquid was diluted and the phage was plated so as to give a considerably low plaque density (10 to 100 pfu/plate). A plaque separated from others was isolated and stored in the same buffer. From this liquid, a plating lysate containing the phage at a high concentration was prepared and in vivo excision was performed in accordance with the instructions attached to ZAP cDNA Synthesis Kit. Thus a plasmid [pBluescriptSK(-)] was prepared from the phage genome.

Then it was digested with restriction enzymes EcoRI and XhoI (manufactured by Takara Shuzo Co., Ltd.) and thus a cDNA insert was isolated and purified. This cDNA insert was fractionated by electrophoresing on a 0.8% agarose gel and blotted onto a nylon membrane filter HybondN+. Then differential hybridization was carried out with the use of pistil and leaf probes as well as single-stranded cDNA probes synthesized by using Oligo dT Primer from the total RNA of anther, germinating seed, root, callus or immature seed. As a result, 6 cDNA clones which were hybridizable with the pistil probe but little with other probes were obtained. Among these clones, one having an insert cDNA of about 1.5 kb was named "RPC213" and employed in the subsequent experiments.

(4) Analysis on Organ-specific Expression of cDNA Clones

1) Northern Hybridization Analysis

The cDNA clone "RPC213" screened in the above 3) was subjected to Northern hybridization to examine the expression patterns and expression levels in various organs. Filters were prepared in the following manner.

First, the secondary structure of the total RNA (20 µg) from each of the organs described in the above 1) was dissociated in accordance with the method of Sambrook et al. (Molecular Cloning, 1982) with the use of deionized Glyoxal and DMSO and then fractionated in a 1% agarose gel. Next, the RNA was blotted onto a nylon membrane Gene Screen Plus (manufactured by DU PONT) by the conventional method. After drying in vacuo at 80° C. for 1 hour, the filter was boiled in 20 mM Tris-Cl (pH 8.0) for 5 minutes to thereby remove Glyoxal therefrom. As a probe, the 1.5 kb EcoRI-XhoI fragment of the above-mentioned CDNA was RI-labeled by using Multiprime Labeling System (manufactured by Amersham). Pre-hybridization and hybridization were carried out in accordance with the manufacturer's instructions attached to the filter. The filters were washed with 2×SSC, 1% SDS and 0.2×SSC, 1% SDS at room temperature each for 5 minutes, then with 0.16×SSC, 1% SDS at 65° C. for 15 minutes twice, and then with 2×SSC at room temperature for 1 minute. Subsequently, the filters were exposed to Kodak X-Omat Film at −70° C. overnight.

As a result, an intense hybridization signal was observed in the lane of mature pistil, weak signals were observed in the lanes of palea and lemma and callus, and very weak signals were observed in the lanes of leaf, anther and immature seed, while other lanes showed no signal, as FIG. 1 shows. Thus, it was clarified by the results of the Northern analysis that the isolated clone relatively strongly expressed in mature pistil and weakly in palea and lemma, and callus but scarcely in leaf, anther and immature seed. The size of the transcripts was estimated to be about 1.6 kb.

2) Reverse Transcription PCR (RT-PCR) Analysis

To analyze the organ-specific expression of the cDNA clone at a higher sensitivity, reverse transcription PCR was carried out by using RNA of various rice organs as templates. By using GENESIS 200 Fluorescence Sequencer (manufactured by DU PONT), the nucleotide sequence of the cDNA inserted into the plasmid pBluescript SK(−) was first partly determined. In accordance with the manufacturer's instructions attached to the Sequencer, T7 DNA polymerase reaction was performed by using M13 and M4 primers (manufactured by Takara Shuzo Co., Ltd.) followed by electrophoresis on a 6% acrylamide gel. Then, the nucleotide sequence was determined from both of the 5'-(EcoRI) and 3'-(XhoI) sides. Based on the DNA nucleotide sequence of about 400 nucleotides (mRNA sense strand) in the 3'-side, the following primers:

```
213S;  5'-CGCTATGGCCCGTTTCAGCT-3', and (SEQ ID NO:5)
213AS; 5'-GTCGTCCTGCCGCTTCATTAC-3'     (SEQ ID NO:6)
``` were synthesized with DNA Synthesizer (manufactured by ABI), purified by OPC Cartilage (manufactured by ABI) and employed in the reverse transcription PCR experiment. It was expected that a product of about 250 bp would be amplified with these primers.

10 μg of the total RNA of each of the above-mentioned organs was mixed with 500 ng of Oligo dT15 Primer (manufactured by Amersham) and the secondary structure thereof was dissociated by treating in 55 μl of the liquid reaction mixture at 70° C. for 10 minutes. After quenching on ice, the mixture was maintained in 100 μl comprising 1×1st strand buffer (manufactured by BRL), 0.5 mM of dNTPmix, 10 mM of DTT, 2 U/μl of RNase inhibitor (RNAguard, manufactured by Pharmacia) and 10 U/μl of reverse transcriptase (Superscript: manufactured by BRL) (each expressed in the final concentration) at 37° C. for 60 minutes. Next, it was treated at 95° C. for 5 minutes to dissociate the RNA-cDNA hybrid and then cooled on ice. The cDNA concentration of this solution was assumed to be 100 ng/μl. Next, the synthesized cDNA of each organ was diluted in 4 series (100 ng/μl, 10 ng/μl, 1 ng/μl, 0.1 ng/μl) and employed as a template in PCR.

PCR was carried out under the following conditions. 1 μl of the cDNA dilution was mixed with 0.5 pmole/μl of primer, 0.2 mM dNTP, 1×PCR buffer and 0.05 U Taq Polymerase (manufactured by Takara Shuzo) (each expressed in the final concentration) to give 20 μl of a reaction mixture. By using Gene Amp 9600 (manufactured by Perkin Elmer), the reaction mixture was subjected to PCR consisting of 3 minutes at 94° C. for 1 cycle, 0.5 minutes at 94° C., 1 minute at 60° C. and 1 minute at 72° C. for 30 cycles and 6 minutes at 72° C. for 1 cycle. The PCR product was electrophoresed on an agarose gel, stained with ethidium bromide and then photographed. Bands were compared with each other in density, and 2 samples showing the same density were estimated to contain the cDNA originating in the above-mentioned gene in the same amount.

Figure 2A:
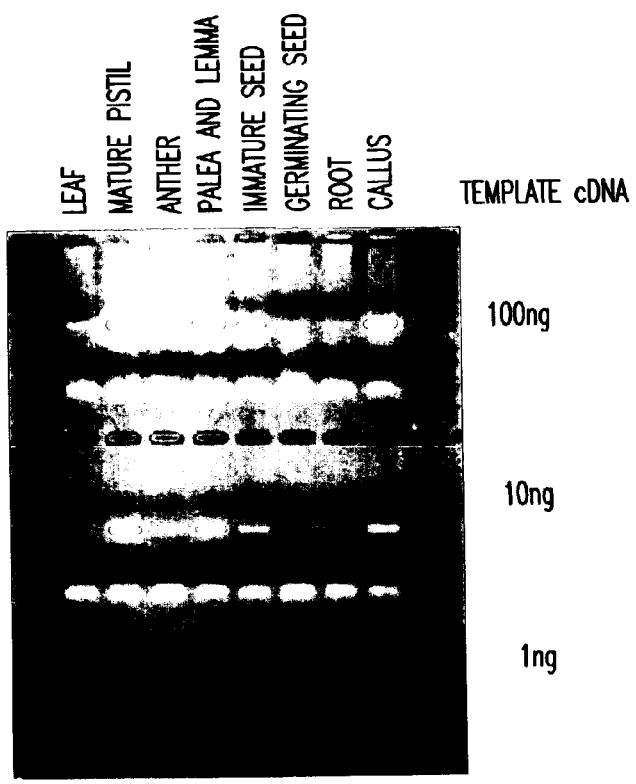
FIG. 2 consists of photographs showing the results of RT-PCR analysis on RPC213.

It was preliminarily confirmed, by using plasmid clones, that the product of the expected molecular weight could be amplified with the primers for RPC213 gene. When reverse transcription PCR was performed by using this primer and 100 ng of cDNA as a template, dense bands of the PCR products were observed in mature pistil, palea and lemma and callus, faint bands were observed in anther and immature seed and exclusively faint bands were observed in leaf, germinating seed and root, as shown in FIG. 2A. Among these organs, mature pistil and palea and lemma showed the PCR product after diluting the template cDNA to 1 ng, while callus, anther and immature seed showed the product only until the template cDNA was reduced to 10 ng. Leaf, germinating seed and root showed no PCR product, when the template cDNA was diluted to be less than 100 ng. When the expression level in mature pistil was taken as 1, it was estimated based on the band density that the expression level in palea and lemma was about 1 to 1/10, those in anther, immature seed and callus were about 1/10 and those in other organs were about 1/100.

Figure 2B:
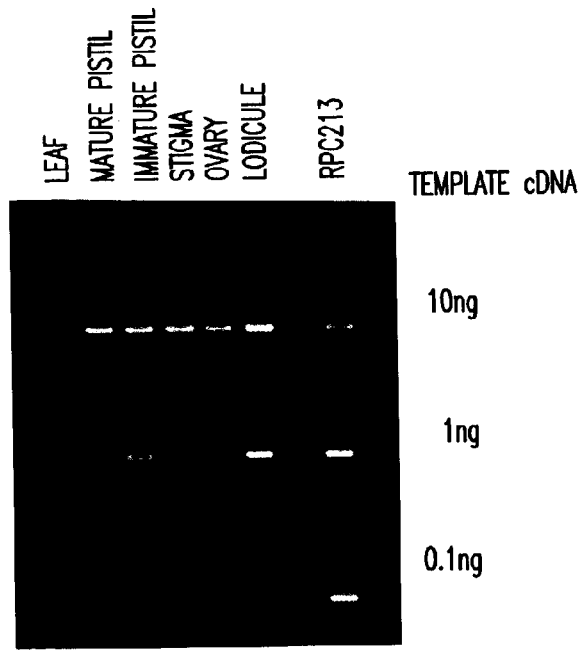

Next, differences in expression levels depending on flower organ sites and development stages were analyzed. cDNAs prepared from whole mature pistil, stigma of mature pistil, ovary of mature pistil, whole immature pistil and lodicule were employed as templates. Also, use was made of leaf cDNA and plasmid DNA as controls. Then PCR was carried out with the use of RPC213-specific primers. As a result, when 10 ng of cDNA was employed as a template, the PCR product was detected in all of the organs other than leaf, as shown in FIG. 2B. Among these organs, immature pistil, stigma and lodicule showed the PCR product even though the template was reduced to 0.1 ng, while mature pistil and its ovary showed the PCR product only until the template was reduced to 1 ng. When the RPC213 expression level in the whole mature pistil was taken as 1, it was estimated based on the above results that the expression level in immature pistil, stigma and lodicule were about 10 and that in ovary was about 1. Namely, the results of the reverse transcription PCR indicate that the RPC213 gene is strongly and predominantly expressed in immature pistil, mature pistil stigma and lodicule but weakly in mature pistil ovary and palea and lemma and scarcely in other organs.

Table 1 summarizes the results of 1) the Northern analysis and the results of 2) the RT-PCR.

TABLE 1

Table 1: Analysis on RPC213 gene expression

| Organ | mature pistil | stigma | ovary | immature pistil | lodicule | palea/ lemma | an- ther | Immature seed | germina- ting seed | leaf | root | root (soil) | callus |
|---|---|---|---|---|---|---|---|---|---|---|---|---|---|
| Northern Analysis | ++ | NT | NT | NT | NT | + | − | ± | − | ± | − | − | + |
| RT-PCR | 1 | 10 | 1 | 10 | 10 | 1~0.1 | 0.1 | 0.1 | 0.01 | 0.01 | 0.01 | NT | 0.1 |

++: strong expression;
+: weak expression;
±: little expression;
−: no expression; and
NT: not analyzed.
RT-PCR: expressed in relative value determined by taking the expression level in mature pistil as 1.

(5) Determination of the Nucleotide Sequence of RPC213

The entire nucleotide sequence of the cDNA clone RPC213 (about 1.5 kb), which is expressed specifically in flower organs, was determined in the following manner with the use of Fluorescence Sequencer (Model 373A, manufactured by Applied Biosystems). Based on the nucleotide sequence information obtained by using the M13 primers (manufactured by Takara Shuzo Co., Ltd.) described above, primers were synthesized and the nucleotide sequence in an undecoded region was determined. By repeating this primer walking procedure, the nucleotide sequence of RPC213 having 1496 bp in total was determined. The reading frame with the largest ORF was identified by the ORF analysis. In this reading frame, polyA signal-like sequences (Heidecker and Messing, Annu. Rev. Plant Physiol. 37, 439–466, 1986) were located about 70 bp and 90 bp downstream of the termination codon TGA. The entire nucleotide sequence of RPC213 is represented by SEQ ID NO:1 in Sequence Listing, though the nucleotide sequence of SEQ ID NO:1 has 1524 bp including a 28 bp segment following the transcription initiation points which was added by reference to the nucleotide sequence of genome clone as will be described hereinafter.

The sequence represented by SEQ ID NO:1 has the following characteristics.

| | |
|---|---|
| nt1, nt2, nt3 | transcription initiation points of the RPC213 gene determined by the primer extension method. |
| nt22–nt24 | the first potential initiation codon of the RPC213 gene. |
| nt295–nt297 | the second potential initiation codon of the RPC213 gene. |
| nt1276–nt1278 | the termination codon of the RPC213 gene. |
| nt1343–nt1348, nt1365–nt1370 | PolyA addition signals. |
| nt1507–nt1524 | PolyA. |

Example 2

Isolation of Promoter (1) Construction of Genomic Library

Genomic DNA was isolated by the SDS-phenol method and purified by the lithium chloride precipitation method from "IR24" rice leaves about 2 months after sowing. As a preliminary test, the DNA was first partly digested with a restriction enzyme MboI (manufactured by Takara Shuzo Co., Ltd.) to determine the digestion conditions which would allow the formation of as many fragments of 16 to 23 kb in apparent size as possible. Next, the genomic DNA was digested under the so determined reaction conditions and subjected to sucrose density gradient centrifugation. Sucrose was dissolved in a buffer (20 mM Tris-HCl pH 8.0, 1 mM EDTA, 200 mM NaCl) to give a gradient of 5 concentrations (10, 17.5, 25, 32.5 and 40%). These sucrose solutions were layered in this order in a centrifugation tube (40PA, manufactured by Hitachi) and finally the partly digested DNA solution was layered on top of the gradient. After centrifuging at 20,000 rpm for 17 hours at 20° C. by using a rotor SRP28 SA (manufactured by Hitachi), the mixture was divided into 80 portions (0.5 ml each) with a peristaltic pump to provide a fraction containing DNA fragments of 16 to 23 kb in the greatest amount. This DNA fraction was then ligated with a vector λDASH II/BamH (manufactured by STRATAGENE) by the action of T4 DNA ligase (manufactured by BOEHRINGER MENNHEIM) and then packaged into phage particles by using Gigapack II Gold packaging extract (manufactured by STRATAGENE). Thus, a rice genomic library was constructed, the size of which was calculated as about $5 \times 10^6$ pfu.

(2) Screening of Clones

About 10,000 pfu of the phage was mixed with *E. coli* SRBP2 for infection and inoculated into a square Petri dish (14×10 cm). After an incubation at 39° C. overnight, a nylon membrane filter Hybond N+ (manufactured by Amersham) was brought into contact with the plaque surface and then processed in accordance with the manufacturer's instructions attached to the filter. The probe was 0.6 kb EcoRI-SalI fragment in the 5'-side of the rice flower organ-specific cDNA (RPC213) which was used after being RI-labeled with the use of Multiprime Labeling System (manufactured by Amersham). Thus, plaque hybridization was carried out. The hybridization and washing were effected under the same conditions as those specified in the above Example 1(3) provided that 1×Denhart's solution and carrier DNAs were not employed. From 100,000 plaques, 6 positive clones were thus selected. Next, phage DNAs were prepared from these plaques. They served as templates in the PCR which was performed with the use of the RPC213-specific primers 213S and 213AS. As a result, the expected product of about 250 bp was found to have been amplified in 2 clones named RPG106 and RPG107.

(3) Subcloning of Region Containing Promoter

DNA was extracted from the above-mentioned 2 RPC213 genomic clones, digested with restriction enzymes SacI and HindIII (manufactured by Takara Shuzo Co., Ltd.) and then the DNA fragments were fractionated in a 0.8% agarose gel.

Also, DNA was isolated and purified by the phenol-SDS method (Komari et al. Theor. Appl. Genet. 77, 547–552, 1989) from paddy rice plants of varieties "Akihikari" and "IR24" about 1 month after sawing. About 5 µg of DNA was digested with SacI and HindIII and electrophoresed similar to the above case. Next, it was blotted onto a nylon membrane filter Hybond-N+ (manufactured by Amersham) and Southern hybridization was performed by using as a probe the above-mentioned cDNA fragment of 0.6 kb having been RI-labeled as in Example 1(4)1).

Hybridization and washing were carried out in accordance with the manufacturer's instructions attached to the filter. As a result, a band of the same size as the total genomic DNA appeared in RPG106. Thus, the SacI fragment (6.0 kb) of RPG106 reacting with the probe was subcloned into the same site of pBluescript. Next, restriction maps (FIG. 3) were formed by using 4 restriction enzymes (BglII, HindIII, SacI and SalI) to further specify the region containing the promoter.

(4) Determination of Whole Nucleotide Sequence of RPG106 SacI-SalI Fragment (5.4 kb)

Figure 3:
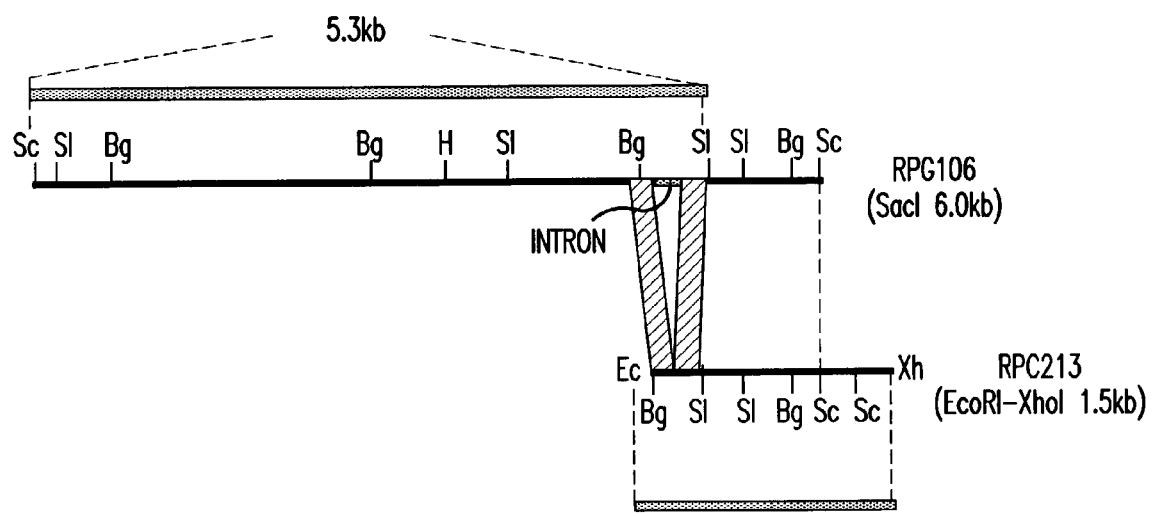
FIG. 3 is a drawing illustrating comparison of the restriction maps of RPC213 and RPG106.

As FIG. 3 shows, the genomic clone RPG106 has four BglII sites. By using these restriction sites, RPG106 was first divided into five fragments. Namely, RPG106 SacI 6.0 kb (pBluescript) was digested with BamHI and BglII to give five fragments, i.e., SacI-BglII 0.7 kb (+pBluescript), BglII 2.1 kb, BglII 2.3 kb, BglII 0.8 kb and BglII-SacI 0.7 kb (multicloning site of +pBluescript). Then the nucleotide sequences of the former 4 fragments were determined. Since the SacI-BglII 0.7 kb fragment still contained pBluescript, this plasmid was cyclized again. Regarding the remaining 3 fragments, plasmids were constructed by inserting these fragments into the BamHI site of pBluescript in the regular direction and vice versa. The fragment BalII 2.1 kb had 2 SpeI sites and 1 XhoI site in it, while the fragment BglII 2.3 kb had 2 EcoRV site, 1 SalI site and 1 SpeO site. Each of these fragments was further subcloned by using these restriction sites to give 14 plasmids in total which covered almost the entire RPG106 SacI 6.0 kb. The nucleotide sequences of both strands of each of these plasmids were determined by using M13 primer (manufactured by Takara Shuzo Co., Ltd.) with Fluorescence Sequencer (Model 373A, manufactured by Applied Biosystems). The nucleotide sequences in regions which could not be decoded by this method were determined by the primer walking method and thus the entire nucleotide sequence of RPG106 SacI-SalI 5.4 kb (total nucleotide sequences 5396 bp) was determined. This nucleotide sequence is represented by SEQ ID NO:3 in Sequence Listing.

The sequence represented by SEQ ID NO:³ has the following characteristics.

| | |
|---|---|
| nt1–nt5369, nt3335–nt5108 | sequences having been confirmed as having promoter activity by GUS. |
| nt4964–nt4969 | TATA box-like sequence. |
| nt4996, 4996, 4997 | transcription initiation points of RPC213 gene determined by the primer extension method. |
| nt5016–nt5018 | first initiation codon of RPC 213 gene. |
| nt5370–nt5372 | second initiation codon of RPC 213 gene. |
| nt5162–nt5242 | intron sequence. |
| nt1–nt6 | restriction enzyme SacI site. |

-continued

| | |
|---|---|
| nt792–nt734, nt2811–nt2816, nt5103–nt5108 | restriction enzyme BglII sites. |
| nt3335–nt3340 | restriction enzyme HindIII site. |

Comparison of the RPC213 gene with the nucleotide sequence of RPC213 cDNA indicated that an intron sequence of 81 bp was located between the first ATG and the second ATG in the RPC213 gene. As shown in the shaded parts in FIG. 3, the nucleotide sequence in the region of about 300 bp from the 5'-terminus to the first SalI site in the cDNA completely agreed with the nucleotide sequence of the genomic DNA RPG106 corresponding to this region except the intron sequence.

(5) Determination of Transcription Initiation Points

To specify the promoter region of RPC213, first, the 5'-terminus of the transcription unit was analyzed by RT-PCR. By reference to nucleotide sequence of the 3'-terminal region (300 bp) of the above-mentioned 2.3 kb BglII fragment of genomic clone RPG106, 4 sense primers (213A, 213B, 213C and 213D) and 1 antisense primer (213Z) were synthesized (FIG. 4). 10 ng of mature pistil cDNA was employed as a template, while 10 ng of leaf cDNA and 10 ng of genomic clone RPG106 BglII 2.3 kb fragment were employed as control. PCR was carried out under the same conditions as employed in Example 1(4)2). As a result, the control leaf cDNA gave no amplification product in any combination of the primers. In contrast, pistil cDNA showed the amplification product of the same size as the genomic clone when primers 213A and 213Z were combined. Based on these results, it was considered that a split point (namely, a transcription initiation point or the 3'-terminus of intron) would be located between 213A and 213B.

Next, transcription initiation points were determined by the primer extension method. First, the primer employed in the RT-PCR:

213Z: 5'-TGCTGGTATGGATGTGATG-3' (SEQ ID NO:7); and an additional primer for the primer extension experiment:

213Z-2: 5'-CTGACGAGGCTGTTGCTG-3' (FIG. 4)(SEQ ID NO:8);

were synthesized. These primers (10 pmole each) were RI-labeled at the 5'-terminus with the use of $[\gamma\text{-}^{32}P]ATP$ according to the manufacturer's instructions attached to MEGARABEL Kit (manufactured by Takara Shuzo CO., Ltd.). 0.1 pmol ($0.3\times10^6$ cpm) of these labeled primers and 50 µg of the total RNA of either immature spikelet (1 to 2 weeks before earing) or leaf were annealed in the presence of 3 U/µl of RNase inhibitor (RNAguard, manufactured by Pharmacia) in a buffer (0.25 M KCl, 2 mM Tris-HCl pH 8.0, 0.2 mM EDTA) in a reaction system of 10 µl at 42° C. for 2 hours. After adding 30 µl of another buffer (66 mM Tris-HCl pH 8.3, 6.6 mM $MgCl_2$, 1.3 mM DTT, 0.66 mM dNTP, 130 µg/ml actinomycin D) and 1 µl (200 units) of a reverse transcriptase (SUPERSCRIPT, manufactured by BRL), the mixture was maintained at 42° C. for 1 hour. Then ethanol and ammonium acetate were added to allow precipitation to occur. After washing the precipitate with 70% ethanol, the product was air-dried and then dissolved in an electrophoresis buffer which was prepared by mixing the reaction termination solution of T7 Sequencing Kit (manufactured by Pharmacia) with 0.1 M NaOH containing 1 mM EDTA (2:1).

Figure 5:
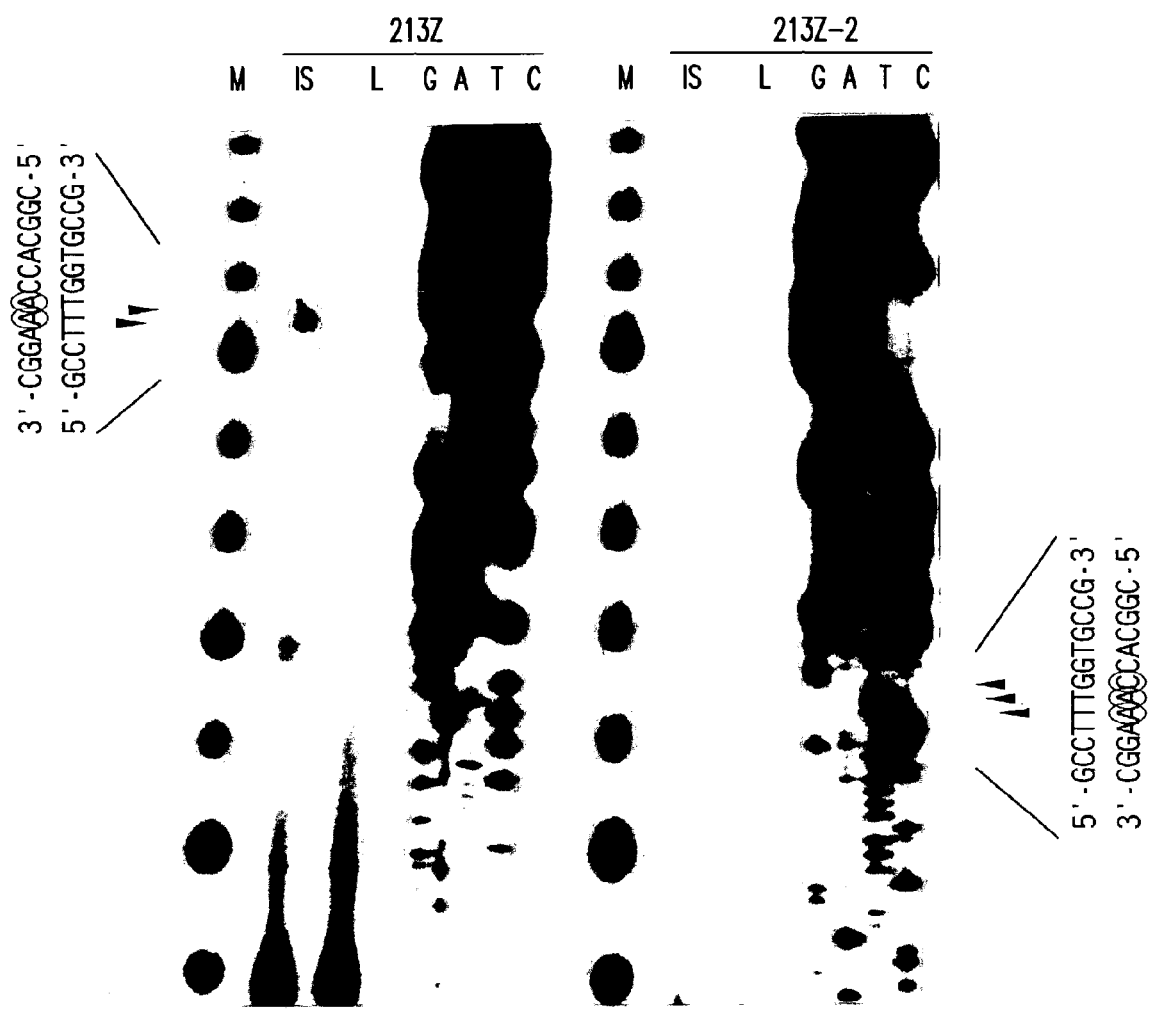
FIG. 5 is a photograph showing the results of primer extension analysis.

Then the whole solution was heated at 95° C. for 3 minutes and then electrophoresed on a 6% agarose gel. By using the same primers, a sequencing reaction was carried out with T7 Sequencing Kit by using a plasmid containing RPG106 BglII 2.3 kb fragment as a template. Then the product thus obtained and the 10 bp and 50 bp ladders (manufactured by BRL), which had been RI-labeled at the terminus via an exchange reaction with the use of [γ-$^{32}$P] ATP according to the manufacturer's instructions attached to MEGARABEL kit (manufactured by Takara Shuzo CO., Ltd.), were electrophoresed simultaneously. The results are shown in FIG. 5. No extension product was obtained from leaf RNA in which the gene was probably not expressed, while 2 bands (in the case of the 213Z primer) and 3 bands (in the case of the 213Z-2 primer) of extension products were detected by using the total RNA of immature spikelet as the template. Comparison with the sequence ladders electrophoresed side by side indicated that the products by these primers were detected at the same position. These results indicated that 3 consecutive transcription initiation nucleotides "CAA" were located between 213A and 213B and the transcription of RPC213 was initiated from the cytosine or adenines. As FIG. 4 clearly shows, a TATA box-like sequence (5'-TATAAAT-3') was located 31 bp upstream of the C (cytosine) of the most upstream transcription initiation point. The distance between this TATA box and the transcription initiation point coincided with genes of other plants (Joshi, Nucleic Acids Res., 156, 6643–6653, 1987). Further, there was an initiation codon (the first ATG) 21 bp downstream of the C of the transcription initiation point. Since the reading frame containing this ATG agreed with the reading frame of the cDNA as described above, it is generally considered that the ATG 21 bp downstream of the transcription initiation point would be the initiation codon. However, it is also considered that the distance between the transcription initiation point and the initiation codon is too short. Accordingly, there is a possibility that the second ATG located 273 bp downstream of the first ATG in the same reading frame might be the actual initiation codon. Moreover, C (cytosine) was located 3 nucleotides upstream of A (adenine) in the first ATG. In contrast, A (adenine) was located 3 nucleotides upstream of A (adenine) in the second ATG, which well agreed with the consensus in nucleotides around the initiation codon of mRNA in eucaryotic cells (Kozak, J. Cell Biol., 108, 229–241, 1989).

Example 3

Figure 6:
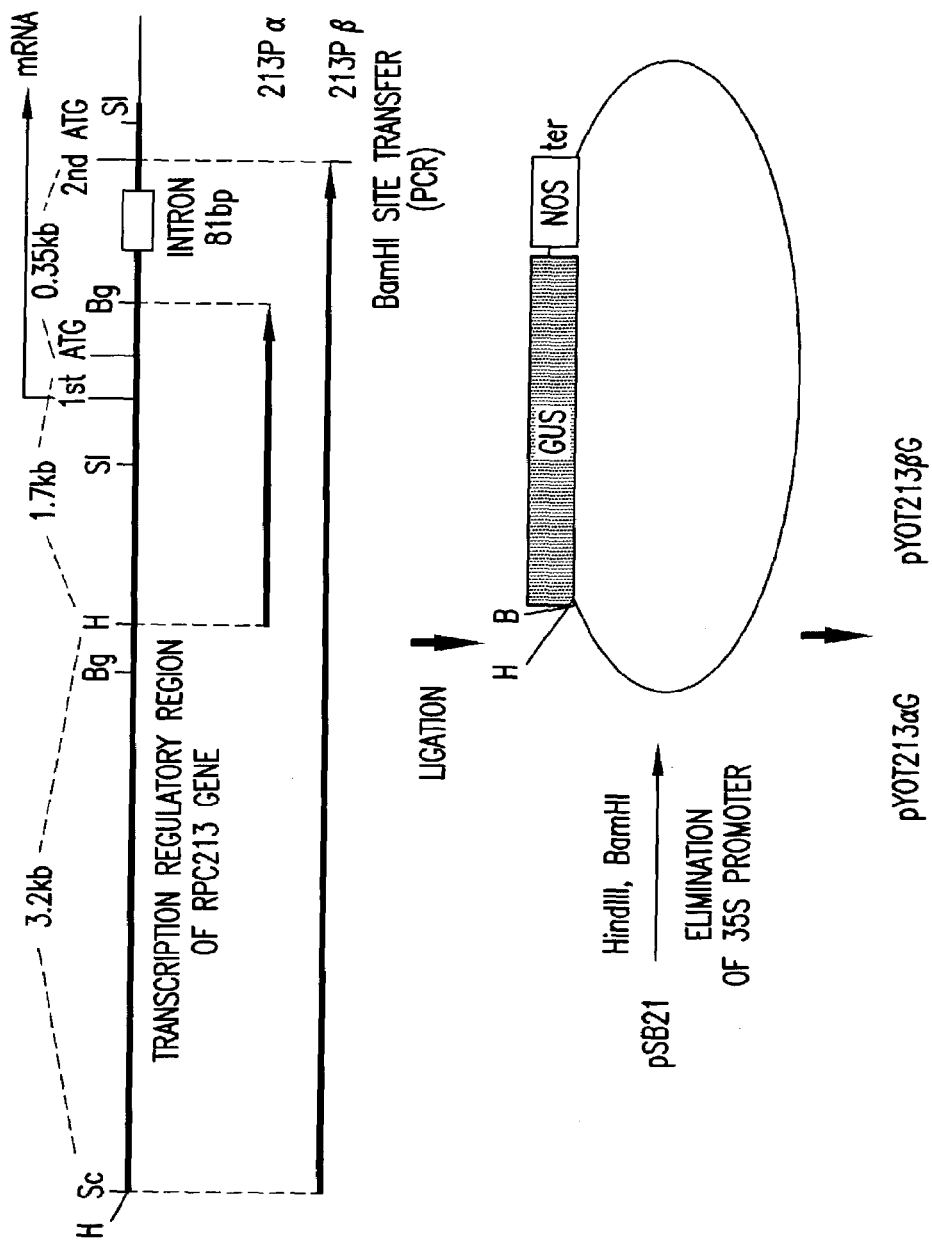
FIG. 6 is a model view showing a procedure for constructing vectors for analyzing the promoter expression.

Analysis of Promoter Expression Site (1) Construction of Vectors for Analyzing Promoter Expression and Transformation of Rice To analyze the expression of the isolated promoter in vivo, vectors having GUS reporter gene linked thereto were constructed in the following manner (FIG. 6). The vector used in this example was pSB21 (Komari et al. Plant J., 10, 165–174, 1996). Use was made of the unique HindIII site and BamHI site located at each termini of 35S promoter contained in this vector.

First, RPC106 SacI 6.0 kbp (pBluescript) was co-digested with HindIII and BglII to isolate a promoter fragment of about 1.8 kbp from the region which precedes the BglII site located 87 bp downstream of the first ATG in the RPC213 gene. This fragment was ligated to vector pSB21 having been digested with the same enzymes to delete the 35S promoter therefrom. The obtained plasmid vector was named pYOT213αG. In pYOT213αG, the first ATG of RPC213 gene and the ATG of the GUS gene were contained in the same reading frame. Therefore, when the translation of the RPC213 gene was initiated from the first ATG, the GUS protein would be translated as a fusion protein.

Second, considering the possibility that the translation of the RPC213 gene might be initiated from the second ATG, another vector was constructed in the following manner to isolate a promoter fragment from a broader region. To amplify a part of the promoter region by PCR, a pair of primers:

```
213P-5H-2:
5'-GACGTGATCCACGGCATTGACG-3',      (SEQ ID NO:9)

213P 2ndATG-Bam:
5'-CGGGGATCCGTTCTCCTCCACCCACGC-3'; (SEQ ID NO:10)
``` were synthesized. 213P-5H-2 matches a region upstream of the unique HindIII site. 213P 2ndATG-Bam matches the nucleotide sequence immediately upstream of the second initiation codon ATG and has a BamHI site. PCR was performed in a reaction system of 100 μl by using these primers (100 pmole each), about 1 μg of DNA (alkali-denatured template RPG106) and Extaq (manufactured by Takara Shuzo Co., Ltd.).

The reaction mixture was subjected to PCR consisting of 3 minutes at 94° C. for 1 cycle; 1 minute at 94° C., 1 minute at 60° C. and 2.5 minutes at 72° C. for 20 cycles; and 6 minutes at 72° C. for 1 cycle. The amplification product was cloned into pCRII (manufactured by Invitrogen) and then the nucleotide sequence was confirmed. This plasmid was digested with HindIII and BamHI and the RPC213 promoter fragment of 2.0 kb was isolated therefrom. Next, the fragment was ligated to the vector pSB21 having been treated by the same enzymes to delete the 35S promoter. The plasmid thus obtained was further digested with HindIII and dephosphorylated. Next, an RPG106 HindIII fragment of 3.3 kb, which was obtained by digesting RPG106 SacI 6.0 kb (pBluescript) with HindIII, was inserted thereinto. The resultant plasmid vector was named pYOT213βG. In this vector, a GUS gene is located downstream of the promoter fragment, and the promoter fragment is composed of about 5.3 kb upstream region from the second ATG of the RPC213 gene. The two vectors thus constructed were each transferred into *Agrobacterium tumefaciens* LBA4404 by tri-parental mating and used in an experiment of the transformation of rice.

The transformation of rice was carried out by using calli developed from immature rice embryo of "Tsukinohikari" in accordance with the method of Hiei et al. (Plant J., 6, 271–282, 1994).

Figure 7A:
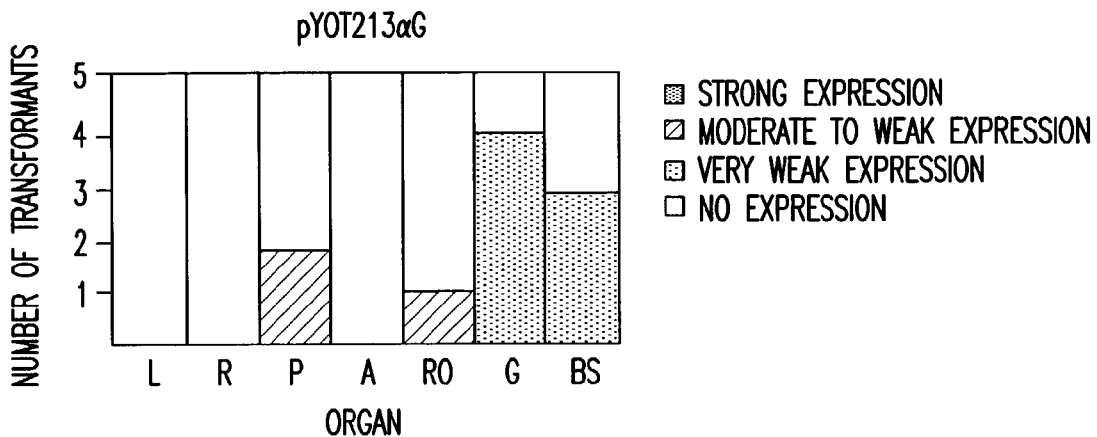
FIG. 7 consists of graphs showing the results of the GUS-analysis with regard to expression sites of 213 promoter.
Figure 7B:
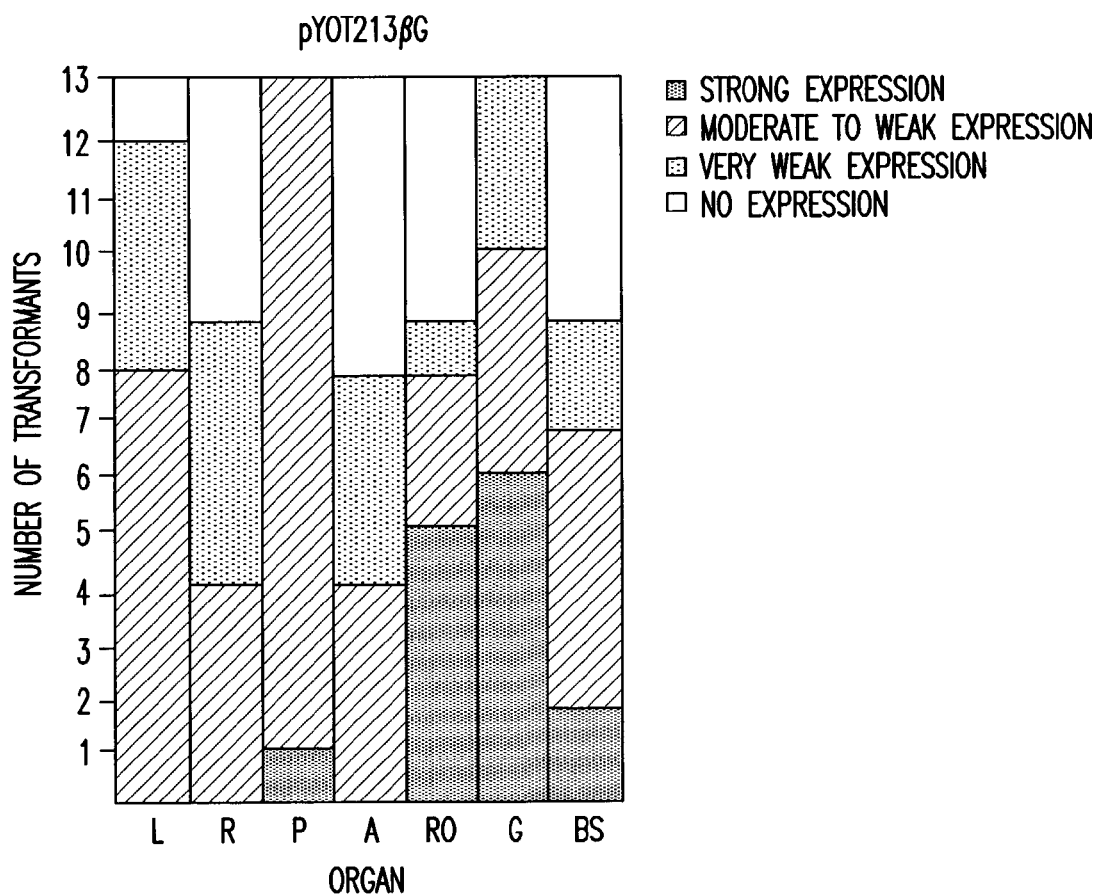

(2) Analysis of Promoter Expression Site by Way of Histological Observation of GUS According to the method of Jefferson et al. (EMBO J., 6, 3901–3907, 1987), various organs (leaf, root, spikelet in earing and spikelet in flowering) of the rice, transfected with pYOT213αG or pYOT213βG, were GUS-stained with the use of X-gluc. (5-bromo-4-chloro-3-indolyl-β-D-glucuronic acid) as the substrate in order to histologically observe the cells under a stereoscopic microscope as well as an optical microscope. Observation was made on organs in spikelet i.e. pistil, anther, lodicule, palea and lemma and spikelet base. The GUS expression level by the promoter was evaluated in 4 grades from "strong (++)" to "less than detection limit (−)" (Table 2). In FIG. 7, black bars stand for "strong expression", shaded bars stand for "moderate to weak expression", dotted bars stand for "very weak expression" and white bars stand for "no expression", while L, R, P, A, RO, G and BS respectively stand for leaf, root, pistil, anther, lodicule, palea and lemma, and spikelet base.

Figure 8A:
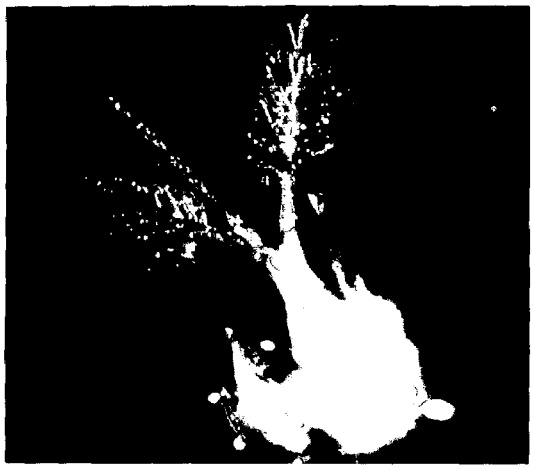
FIG. 8 consists of photographs showing exemplary results of the GUS-analysis with regard to expression sites of 213 promoter.
Figure 8B:
Figure 8C:
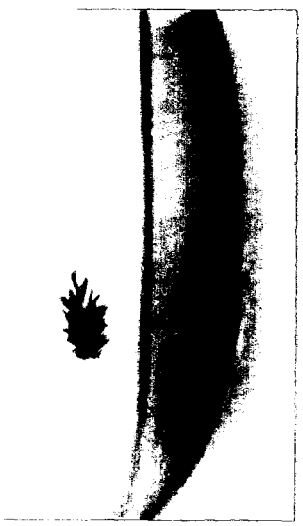
Figure 8D:

As a result, many individuals transfected with pYOT213αG were not stained with GUS in any organ examined. However, 5 individuals showed the expression of the GUS gene by the promoter activity in at least one of the organs. Among these individuals, pYOT213αG-17 showed GUS expression in pistil and lodicule and very weak expression in palea and lemma and spikelet base (Table 2). These results generally agreed with the results of Northern hybridization and RT-PCR. pYOT213αG-4 showed the GUS expression specifically in pistil (Table 2). The expression in pistil was observed around the border of stigma and ovary (FIG. 8A). None of these 5 individuals showed the GUS expression in leaf, root and anther. 2 individuals showed the expression in pistil, one showed in lodicule (FIG. 7). In addition, very weak expression was observed in palea and lemma in 4 individuals and in spikelet base in 3 individuals.

also observed in palea and lemma, anther, lodicule and spikelet base (FIG. 8B). pYOT213βG-17 showed very weak or no expression in leaf and root (FIG. 8D) but relatively strong expression in pistil (FIG. 8C). In pistil of the individuals transfected with pYOT213βG, the GUS expression was observed mainly in the stigma, i.e., stigma axis and hairy tissues in stigma (FIG. 8B and C). The results of the examination of the GUS expression in the organs are summarized in FIG. 7, which indicated that no individual showed strong expression in leaf or root. About ½ or more of the individuals showed moderate to weak expression in leaf, while about ⅓ or less of the individuals showed moderate to weak expression in root. The remaining individuals showed very weak or no expression in leaf or root. In flower organs, in contrast, strong promoter activity was observed in all organs except anther (i.e., pistil, lodicule, palea and lemma and spikelet base). In particular, all of the 13 individuals showed definite GUS expression in pistil and one of them showed an intensely blue GUS-stain, thus indicating strong expression. In lodicule and palea and lemma, the expression of the GUS gene by the promoter

TABLE 2

Table 2: Analysis of GUS expression site by 213 promoter

| | | Organ of rice transformant | | | | | | |
|---|---|---|---|---|---|---|---|---|
| Vector | Plant No. | leaf | root | pistil | anther | lodicule | palea/ lemma | spikelet base |
| pYOT213αG | 4 | − | − | + | − | − | − | − |
| | 6 | − | − | − | − | − | ± | − |
| | 17 | − | − | + | − | + | ± | ± |
| | 23 | − | − | − | − | − | ± | ± |
| | 28 | − | − | − | − | − | ± | ± |
| pYOT213βG | 3 | ± | ± | + | + | − | ++ | + |
| | 4 | + | + | + | + | ++ | ++ | + |
| | 6 | + | + | ++ | ± | ± | + | ± |
| | 7 | ± | ± | + | ± | ++ | ++ | + |
| | 8 | − | − | + | − | + | + | ± |
| | 11 | + | + | + | + | ++ | ++ | ++ |
| | 13 | + | + | + | − | + | + | + |
| | 15 | + | ± | + | ± | − | + | − |
| | 16 | ± | ± | + | ± | − | ± | − |
| | 17 | ± | − | + | − | − | ± | + |
| | 20 | + | − | + | − | + | + | − |
| | 22 | + | ± | + | + | ++ | ++ | ++ |
| | 23 | + | − | + | − | ++ | ++ | − |

++: strong expression;
+: moderate to weak expression;
±: little expression; and
−: no expression.

On the other hand, 5 individuals (pYOT213βG-3, 7, 8, 16 and 17) among 13 individuals transfected with pYOT213βG showed no or very weak GUS expression in leaf and root, and showed the GUS expression in flower organ, namely, they showed the flower organ-specific promoter activity (Table 2). Among them, 2 individuals (pYOT213βG-7 and 8) presented results well agreeing the results of Northern hybridization and RT-PCR, i.e., relatively strong GUS expression in pistil and lodicule and very weak expression in anther. The other eight transformants than those showing the flower organ-specific expression also showed relatively strong promoter activity in flower organs even though they showed the GUS expression in leaf and root (Table 2). For example, pYOT213βG-6, which showed the GUS expression in leaf and root, exhibited stronger expression in pistil than in these organs. In this individual, weak expression was activity was observed in about ⅔ of the all individuals and more than ½ thereof (5 individuals for lodicule and 6 individuals for palea and lemma) showed strong GUS expression. Also, 2 individuals showed strong expression in spikelet base.

Based on these results, it has been clarified that these two DNA fragments ligated to the GUS gene have promoter activities predominant in flower organs. It is also found that 213β having a longer fragment has the stronger activity. Since these promoter fragments are similar with each other in organ-specificity even though the promoter activity of 213β is higher than that of 213α, it is expected that a nucleotide sequence regulating the expression level (contributing to enhanced expression) of the RPC213 promoter will be contained in the SacI-HindIII 3.3 kb fragment in the 5'-side from 213α, which is contained in the nucleotide sequence of 213β but not in the nucleotide sequence of 213α, or in the DNA sequence from BglII to the second ATG in the 3'-side from 213α. The latter sequence is seemingly the more likely candidate.

INDUSTRIAL APPLICABILITY

The present invention makes it possible to genetically manipulate flower organs such as pistil and lodicule.

The invention claimed is:

1. An isolated DNA fragment comprising a nucleic acid sequence of positions 3335 to 5108 in SEQ ID NO:3, wherein said DNA fragment has flower organ-specific promoter activity.

2. A isolated DNA fragment comprising a nucleic acid sequence of positions 1 to 5369 in SEQ ID No:3, wherein said DNA fragment has flower organ-specific promoter activity.

3. An isolated DNA fragment comprising a nucleic acid sequence of positions 3335 to 5369 in SEQ ID NO:3, wherein said DNA fragment has flower organ-specific promoter activity.

4. An isolated DNA fragment comprising a nucleic acid sequence of positions 1 to 5108 in SEQ ID NO:3, wherein said DNA fragment has flower organ-specific promoter activity.

5. A chimeric DNA sequence comprising a DNA fragment having a flower organ-specific promoter activity comprising a nucleic acid sequence of positions 3335 to 5108 in SEQ ID NO:3, and a structural gene under control of the promoter activity.

6. A transformation vector having a chimeric DNA sequence comprising a DNA fragment having a flower organ-specific promoter activity comprising a nucleic acid sequence of positions 3335 to 5108 in SEQ ID NO:3, and a structural gene under control of the promoter activity.

* * * * *